United States Patent
Ts'o et al.

[11] Patent Number: 5,962,237
[45] Date of Patent: Oct. 5, 1999

[54] METHOD OF ENRICHING RARE CELLS

[75] Inventors: Paul O. P. Ts'o, Ellicott City; Zheng-Pin Wang, Towson; Stephen A. Lesko, Baltimore; William G. Nelson, Towson; Alan W. Partin, Baltimore, all of Md.

[73] Assignee: The Johns Hopkins University School of Medicine, Baltimore, Md.

[21] Appl. No.: 08/832,468

[22] Filed: Apr. 2, 1997

Related U.S. Application Data

[60] Provisional application No. 60/014,929, Apr. 5, 1996.

[51] Int. Cl.$^6$ .................. G01N 33/574; G01N 33/53; G01N 9/30; B01D 33/15
[52] U.S. Cl. .................. 435/7.23; 435/2; 435/6; 435/7.24; 210/781; 210/782; 422/72; 422/101; 422/102
[58] Field of Search .................. 435/7.23, 6, 172, 435/69.3, 70.2, 2, 7.21, 7.24, 5; 210/781, 782; 422/72, 101, 102

[56] References Cited

U.S. PATENT DOCUMENTS

| | | | |
|---|---|---|---|
| 4,255,256 | 3/1981 | Ferrante et al. | 210/730 |
| 4,751,001 | 6/1988 | Saunders | 210/516 |
| 4,888,278 | 12/1989 | Singer | 435/6 |
| 4,927,750 | 5/1990 | Dorn | 435/2 |
| 5,153,117 | 10/1992 | Simons | 435/6 |
| 5,273,883 | 12/1993 | Saiki et al. | 435/6 |
| 5,432,054 | 7/1995 | Saunders et al. | 435/2 |
| 5,437,987 | 8/1995 | Teng | 435/7.25 |
| 5,529,903 | 6/1996 | Kübler et al. | |
| 5,541,072 | 7/1996 | Wang et al. | |
| 5,612,185 | 3/1997 | Uhr et al. | |
| 5,646,001 | 7/1997 | Terstappen et al. | |
| 5,648,223 | 7/1997 | Vlasselaer | 435/7.23 |

FOREIGN PATENT DOCUMENTS

| | | |
|---|---|---|
| 91 07660 | 5/1991 | WIPO . |
| 94 02646 | 2/1994 | WIPO . |
| 94 09820 | 5/1994 | WIPO . |
| 94 26104 | 11/1994 | WIPO . |
| 95 03431 | 2/1995 | WIPO . |
| 95 08646 | 3/1995 | WIPO . |

OTHER PUBLICATIONS

Griwatz et al. J. Immunological Methods. 183, 251–265, 1995.

(List continued on next page.)

*Primary Examiner*—Paula K. Hutzell
*Assistant Examiner*—Lin Sun-Hoffman
*Attorney, Agent, or Firm*—Leydig, Voit & Mayer, Ltd.

[57] ABSTRACT

A method for enriching cancer cells such as prostate cancer cells in a bodily fluid sample is disclosed comprising (a) obtaining the sample comprising cancer cells and non-rare cells; (b) subjecting the sample to multiple density gradient separation comprising a first density gradient and a second density gradient, wherein the second density gradient is greater than the first density gradient, and producing a first fluid comprising an increased concentration of cancer cells of a first density, and a second fluid comprising an increased concentration of cancer cells of a second density, wherein the second density is greater than the first density; wherein subjecting the sample to multiple density gradient separation includes producing a plasma layer, a first interface layer, a first gradient layer, a second interface layer, a second gradient layer, and a cell pellet; wherein producing the first fluid includes combining the first interface layer and the first gradient layer and forming a first suspension; and wherein producing the second fluid includes combining the second interface layer and the second gradient layer and forming a second suspension; (c) subjecting said second fluid comprising the second suspension to a binding agent that binds non-rare cells; and (d) removing the bound non-rare cells from the second fluid to provide a second fluid enriched with the greater density cancer cells.

37 Claims, 6 Drawing Sheets

OTHER PUBLICATIONS

Prenatal Diagnosis, "Enrichment of Fetal Cells from Maternal . . . Analysis", Busch, J., et al., vol. 14, 1994, pp. 1129–1140.

Experimental Cell Research, "The Experimental Homologous and . . . T–Lymphocytes", Lesko, et al., vol. 219, 1995, pp. 499–506.

Cytometry, "Ouantitation and Mapping of Integrated Human . . . System", Callahan, D.E., et al., vol. 13, 1992, pp. 453–461.

Cancer Research, "Nuclear Matrix Protein Patterns in Human . . . Cancer", Partin, A.W., et al., vol. 53, Feb. 1993, pp. 744–746.

Urology, "Molecular Staging of Prostate Cancer with the Use . . . Assay", Katz, A., et al., vol. 43, No. 6, Jun. 1994, pp. 765–775.

Physician's NewScan, "Centocor's Rred Identifies One Cell in Millions", order No. 256588#, 1 page article.

Jrnl of Clinical Oncology, "Detection of Circulating Tumor . . . Cancer ", Seiden, et al., vol. 12, No. 12, Dec. 1994, pp. 2634–2639.

Jama, "Detection of Organ–Confined Prostate Cancer is . . . Screen Ing", Catalona, et al., vol. 270, No. 8, Aug. 1993, pp. 948–954.

Jrnl of Urology, "The Clinical Usefulness of Prostate Specific . . . 1994", Partin, A.W., et al., vol. 152, Nov. 1994, pp. 1358–1368.

The New England Jrnl of Med., "Measurement of Prostate–Specific . . . Cancer", Catalona, et al., vol. 324, No. 17, pp. 1156–1164.

The Jrnl of Urology, "Demonstration of a Rational Strategy . . . Therapy", Sanda, et al., vol. 151, Mar. 1994, pp. 622–628.

The Johns Hopkins Univ. School of Med., Dept. of Urology, "Prostate Cancer: The Magnitude . . . States", Carter, et al., pp. 1–7.

Cytometry, "Estimation of Fetal Hemoglobin Levels in Individual . . . Cytometry", Horiuchi, et al., vol. 20, 1995, pp. 261–267.

British Jrnl of Hematology, "Immunochemical Estimation of Haemoglobin . . . Analysis", Thorpe, et al., vol. 87, 1994, pp. 125–132.

Jrnl of Clinical Oncology, "Prostate–Specific Antigen as a . . . Cancer", Kelly, et al., vol. 11, No. 4, Apr. 1993, pp. 607–615.

Biochemical & Biophysical Research Comm., "Molecular Cloning and CDNA's", Reigman, et al., vol. 155, No. 1, Aug. 1988, pp. 181–188.

Urology, "Detection of Intact Prostate Cancer Cells in the . . . Cancer", TS'O, et al., vol. 49, No. 6, Jun. 1997, 6 pages.

Clinical Chemistry, "Detection of Prostatic Cells in Peripheral . . . Antigen", Jaakkola, et al., vol. 41, No. 2, 1995, pp. 182–186.

Dynal, Dynabeads® Biomagnetic Separation Technology, 17 pages from various catalogues.

Leather, A.J.M. et al.; "Detection . . . colorectal cancer", Br. J. Surg., vol. 80(6): pp. 777–780 (1953).

Fornabaio, M. et al.; "Selective fractionation . . . centrifugation", Cancer Letters, vol. 44: pp. 185–190 (1989).

Minami, R. et al.; "Gradient Separation . . . Tumor Diagnosis", Acta Cytologica, vol. 22(6): pp. 584–588 (1978).

Nagasawa, T. et al.; "Enrichment . . . Density Gradients", Acta Cytologica, vol. 27(2): pp. 119–123 (1983).

Grunt, Th. W. et al.; "Separation . . . gradient centrifugation", Cancer Letters, vol. 58: pp. 7–16 (1991).

Fleming, J.A. et al.; "A critical . . . from the blood", J. clin. Path., vol. 20: pp. 145–151 (1967).

Spalsbury, C. et al.; "Discontinuous . . . Cytologic Applicability", Acta Cytologica, vol. 17(6): pp. 522–532 (1973).

Schwartz, R. et al.; "Assay . . . Circulating Blood", J Cancer Res Clin Oncol, vol. 109: pp. 122–129 (1985).

Hamburger, A.W. et al.; "Percoll density . . . malignant effusions", Br. J. Cancer, vol. 51: pp. 253–258 (1985).

Cytogenet Cell Genet, Construction of a Panel of Chromosome . . . in Situ, Koch, J., et al., vol. 71, 1995, pp. 142–147.

Advances In Brief, "Sensitive Nested Reverse . . . Antigen–Based Assays[1]", Israeli, R.S., et al., Sep. 24, 1994, pp. 6306–6310.

Hum Genet, "Use of the Primed in Situ Labelling (Prins) Technique . . . X and Y", Pellestor, et al., vol. 95, 1995, pp. 12–17.

Dr. Ts'o Abstract for American Urological Assoc. Meeting, Orlando, Fl., May 1996, "Harvest of Circulating Prostate . . . Cancer".

Blood, "Enrichment of Erythrocytes of Fetal . . . Hemoglobinopathies", Boyer, et al., vol. 46, No. 6, Jun., 1976, pp. 883–897.

Urology, "Selection of Men at High Risk for Disease . . . Prostatectomy", Partin, et al., vol. 45, No. 5, May 1995, pp. 831–837.

//<br>

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 72 base pairs
      (B) TYPE: nucleic acid
      (C) STRANDEDNESS: single
      (D) TOPOLOGY: linear (ii) MOLECULE TYPE: other nucleic acid (synthetic DNA)

(xi) SEQUENCE DESCRIPTION: SEQ ID NO: 1:

```
TGGCTGTGCG CTGGGGCGCT GGTGCTGGCG GGTGGCTTCT TTCTCCTCGG CTTCCTCTTC     60

GGGTGGTTTA TA                                                          72
```

(2) INFORMATION FOR SEQ ID NO:2:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO: 2:

```
AGTGTCTATG AAACATATGA GTTGGTGGAA AAGTTTTATG ATCCAATGTT               50
```

(2) INFORMATION FOR SEQ ID NO:3:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO: 3:

```
GGTCCTCACA GCTGCCCACT GCATCAGGAA CAAAAGCGTG ATCTTGCTGG GTCGGCACAG     60
```

(2) INFORMATION FOR SEQ ID NO:4:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO: 4:

```
CGCTGGACAG GGGGCAAAAG CACCTGCTCG GGTGATTCTG GGGGCCCACT TGTCTGTAAT     60
```

(2) INFORMATION FOR SEQ ID NO:5:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: Nucleic acid (synthetic DNA)

(xi) SEQUENCE DESCRIPTION: SEQ ID NO: 5:

```
GCTGTGGCAT TTTCAGGTGG AGATTTCAAG CGATTTGAGG ACAATTGCAG               50
```

(2) INFORMATION FOR SEQ ID NO:6:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO: 6:

```
GTGTTTGAGC TAGCCAATTC CATAGTGCTC CCTTTTGATT GTCGAGATTA               50
```

-continued (2) INFORMATION FOR SEQ ID NO:7:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO: 7:

TCTTCCTCAC CCTGTCCGTG ACGTGGATTG GTGCTGCACC CCTCATCCTG TCTCGGATTG     60

(2) INFORMATION FOR SEQ ID NO:8:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO: 8:

CAGGCTGGGG CAGCATTGAA CCAGAGGAGT TCTTGACCCC AAAGAAACTT CAGTGTGTGG     60

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (synthetic DNA)

(x) PUBLICATION INFORMATION:
        (A) AUTHORS: Meyne, Julianne
            Moyzis, Robert K.
        (B) TITLE: In Situ Hybridization Protocols
        (C) JOURNAL: Meth. in Mol. Biol.
        (D) VOLUME: 33
        (F) PAGES: 63-74
        (G) DATE: 1994

(xi) SEQUENCE DESCRIPTION: SEQ ID NO: 9:

GTACTCACAC TAAGAGAATT GAACCACCGT                                       30

(2) INFORMATION FOR SEQ ID NO:10:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO: 10:

ATGTGTGTAC TCACACTAAG AGAATTGAAC CACCGTTTTG AA                         42

METHOD OF ENRICHING RARE CELLS

This application claims the benefit of U.S. Provisional Patent Application Ser. No. 60/014,929, filed Apr. 5, 1996, which is incorporated by reference in its entirety.

TECHNICAL FIELD OF THE INVENTION

The present invention relates to a method of enriching rare cells in a fluid containing a mixture of rare cells and non-rare cells, and particularly to a method of enriching rare non-blood cells such as cancer cells, from bodily fluids, such as blood.

BACKGROUND OF THE INVENTION

There has been a growing interest in enriching rare cells (e.g., for subsequent isolation and characterization) over the past several years. This may be attributed at least in part to the recognition that rare cells, such as cancer cells, can provide information that is helpful in the diagnosis and/or treatment of various medical conditions.

The desire to enrich cancer cells is based in part on the knowledge that a majority of cancer deaths occur due to the metastasis of tumors. As such, the presence of carcinoma cells in the peripheral blood is an indication of cancer cell spread, and enriching such cancer cells would be of great diagnostic benefit. This need is particularly acute in prostate cancer, wherein approximately two-thirds of such cancers are clinically localized at the time of diagnosis, but only about half of these prove to be confined to the prostate at the time of surgery. Thus, nearly one-third to one-half of cancers have spread beyond the prostate when first identified, cancers which could be detected at any earlier stage if accurate, highly sensitive enrichment methods were available.

Much of the activity with respect to the early detection of prostate cancer has centered around the usefulness of serum prostate specific antigen (PSA). However, PSA is organ specific and not cancer specific, and is produced by normal, benign, and malignant prostate epithelium. As a result, the positive predictive value for PSA as a screen for prostate cancer is generally less than 50 percent.

Additionally, the maximal level of cancer cells in the peripheral blood has been estimated to be two in $10^7$ leukocytes. Fidler, *Cancer Res.*, 50, 6130 (1990). Thus, while studies have suggested that prostate cancer cells circulate in the bloodstream of men with advanced disease, it is difficult to detect these few circulating cancer cells.

Methods for separating and detecting cancer cells have included, for example, using immunomagnetic beads and the polymerase chain reaction (e.g., Hardingham et al. *Cancer Res.*, 53, 3455 (1993)), using density gradient gels (e.g., U.S. Pat. No. 4,255,256), or using density gradient centrifugation followed by immunological separation to bind the cancer cells (e.g., Griwatz et al., *J. Immunol. Methods.*, 183, 251–265 (1995)).

These methods have been generally unsatisfactory as they lack the efficiency and sensitivity to separate the few cancer cells in a blood sample. Additionally, these methods may provide low cell recovery, since the highly fragile cancer cells can be damaged during the separation process and/or the relatively sticky cancer cells can become inappropriately bound during the separation process.

For example, conventional processes utilize "positive selection", wherein a rare cell is bound to a binding agent such as an antibody, and the bound rare cell is separated from the non-rare cells. Thereafter, the rare cell is separated from the antibody by heat or other suitable means, which can damage or destroy the rare cell, making it difficult to detect and/or culture. Additionally, or alternatively, some processes involve concentrating cancer cells by centrifugation. However, since some cancer cells are fragile and/or tend to stick to surfaces onto which they come into contact, these processes can also damage or destroy the rare cells, which is undesirable as described above. Furthermore, some processes provide for "fixing" the cells during the separation process, thus rendering them unsuitable for culturing or PCR analysis.

In view of the foregoing, there exists a need for an efficient, highly sensitive and highly reproducible method for enriching rare cells from a population of cells. There is also a need for a method that can minimize damage to those rare cells that are fragile and/or sticky.

The present invention provides for ameliorating at least some of the disadvantages of the prior art. These and other advantages of the present invention will be apparent from the description as set forth below.

SUMMARY OF THE INVENTION

The present invention provides a method for enriching rare cells in a fluid comprising the rare cells (that are preferably rare non-blood cells) and non-rare cells. An embodiment of the method comprises (a) subjecting the fluid comprising rare cells and non-rare cells to density gradient separation and producing a fluid comprising an increased concentration of rare cells; (b) subjecting the fluid having an increased concentration of rare cells to an agent that binds non-rare cells; and (c) removing the bound non-rare cells from the fluid so as to enrich the rare cells in the fluid.

Another embodiment of the method comprises (a) subjecting the fluid to density gradient separation and producing a first fluid comprising an increased concentration of rare cells and a second fluid comprising an increased concentration of rare cells; (b) subjecting at least one of said first fluid and said second fluid to an agent that binds non-rare cells; and (c) removing the bound non-rare cells from the first and/or the second fluid so as to enrich the rare cells in the fluid(s). Typically, after the bound non-rare cells are removed from the first and/or the second fluid, the rare cell-containing first fluid and second fluid are combined.

Embodiments of the present invention also provide for further processing the rare cells. For example, rare cells (such as cancer cells) can be identified and/or cultured. Illustratively, in some embodiments involving identification, specific antigens in and/or on the cancer cells can be detected. Additionally, or alternatively, the expression of specific nucleic acids can be detected, and, if desired, chromosomal changes (e.g., aneuploidy) can be detected. In one embodiment, an identification protocol includes combination staining (involving immunocytochemistry staining) and fluorescent in situ hybridization (FISH). Embodiments of the invention also provide improved methods of diagnosis, staging, and monitoring of cancer in a patient.

The present invention further provides certain nucleic acid sequences suitable as probes for cancer cells, particularly prostate cancer cells. The present invention further provides compositions comprising the rare cells isolated by the various processes.

DETAILED DESCRIPTION OF THE PREFERRED EMBODIMENTS

Figure 1:
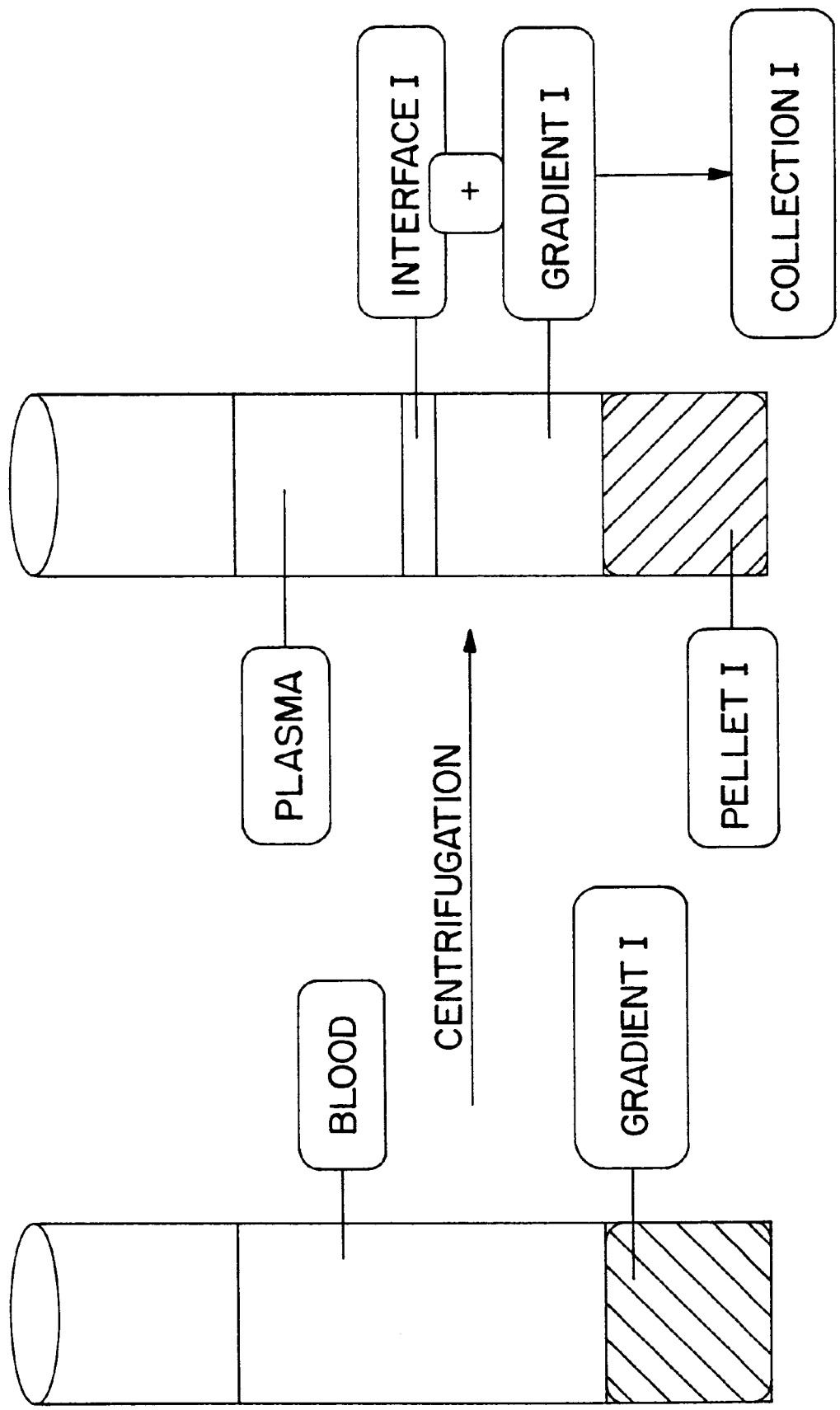
FIG. 1 schematically depicts a density gradient column before (on the left) and after (on the right) centrifuging a fluid sample (e.g., blood). Four regions are formed after centrifugation: Plasma I, Interface I, Gradient I, and Cell Pellet I. Interface I and Gradient I are combined to provide a first fluid including an increased concentration of rare cells, referred to below as the Collection I fluid. Plasma I and Pellet I can be combined and centrifuged to form another column having four regions.

The present invention provides a sensitive, economical, and reproducible method for enriching rare cells in a fluid comprising rare and non-rare cells. In accordance with the invention, a fluid comprising rare and non-rare cells is subjected to density gradient separation, before producing at least one fluid comprising an increased concentration of rare cells. The fluid comprising an increased concentration of rare cells is subjected to a "negative selection process" comprising contacting the fluid with an agent which binds the non-rare cells. The bound non-rare cells are then separated from the fluid, providing a fluid enriched with the rare cells. The rare cells can be further processed, e.g., to identify, characterize, and/or culture the cells. For example, the rare cells can be identified and characterized to detect one or more types of cancer. Embodiments of the present invention provide for monitoring the progress, or regression, of cancer during or after therapy, and are particularly useful for monitoring prostate cancer in men.

In an embodiment, a fluid comprising rare and non-rare cells is subjected to density gradient separation, before producing a first fluid comprising an increased concentration of rare cells and a second fluid comprising an increased concentration of rare cells. This first fluid and/or second fluid is subjected to the negative selection process comprising contacting the fluid(s) with an agent which binds the non-rare cells. The bound non-rare cells are then separated from the fluid(s), providing the fluid(s) enriched with the rare cells.

Additionally, since embodiments of the method according to the invention can be carried out while minimizing stress to those rare cells that are fragile and/or sticky, the rare cells can be recovered essentially unscathed. This is especially desirable, as the live recovered rare cells have a variety of uses, e.g., for studies of the whole cell and/or cell culturing. Moreover, embodiments of the method allow different forms of rare cells in the same sample (e.g., "light" and "heavy" rare cells) to be processed differently, thus allowing a great proportion, if not substantially all, of the rare cells to be recovered, while reducing the presence of the non-rare cells in the rare cell-enriched fluid.

An embodiment of the invention provides a method for enriching rare cells in a fluid sample comprising rare cells and non-rare cells, comprising (a) obtaining the sample comprising rare cells and non-rare cells; (b) subjecting the fluid sample to density gradient separation and producing a fluid having an increased concentration of rare cells; (c) subjecting the fluid having an increased concentration of rare cells to a binding agent that binds non-rare cells; (d) removing the bound non-rare cells from the fluid to provide a fluid enriched with rare cells. Preferably, the rare cells are cancer cells. In some embodiments, the non-rare cells comprise blood cells, i.e., white blood cells (leukocytes) and/or red blood cells (erythrocytes).

In one embodiment of the invention, a method for enriching rare non-blood cells in a fluid sample comprising rare non-blood cells and non-rare cells, wherein the ratio of the rare non-blood cells to the non-rare cells is at least about 1:100,000, comprises (a) obtaining the fluid sample comprising rare non-blood cells and non-rare cells; (b) subjecting the fluid sample to density gradient separation and producing a first fluid (I) comprising an increased concentration of rare non-blood cells, and a second fluid (II) comprising an increased concentration of rare non-blood cells; (c) subjecting at least one of said first fluid (I) and said second fluid (II) to a binding agent that binds non-rare cells; (d) removing the bound non-rare cells from the first fluid (I) and/or the second fluid (II) to provide a first fluid (Ia) enriched with rare non-blood cells and/or a second fluid (IIa) enriched with rare non-blood cells.

In another embodiment, a method for enriching rare non-blood cells in a fluid sample comprising rare non-blood cells and non-rare cells, wherein the ratio of the rare non-blood cells to the non-rare cells is at least about 1:100,000, comprises (a) obtaining the fluid sample comprising rare non-blood cells and non-rare cells; (b) subjecting the fluid sample to density gradient separation and producing a fluid comprising an increased concentration of rare non-blood cells; (c) subjecting the fluid comprising an increased concentration of rare non-blood cells to a binding agent that binds non-rare cells; (d) removing the bound non-rare cells from the fluid to provide a fluid enriched with rare non-blood cells.

Another embodiment according to the invention provides a method for enriching cancer cells in a blood sample comprising (a) obtaining the blood sample comprising cancer cells; (b) subjecting the blood sample to density gradient separation and producing a first fluid comprising an increased concentration of cancer cells of a first density, and a second fluid comprising an increased concentration of cancer cells of a second density, wherein the second density is greater than the first density; (c) subjecting said second fluid to a binding agent that binds white blood cells and/or red blood cells; (d) removing the bound white and/or red blood cells from the second fluid to provide a second fluid enriched with the greater density cancer cells. In some embodiments, the second fluid comprising an increased concentration of cancer cells of a second density is subjected to a binding agent that binds white blood cells and red blood cells, and the bound blood cells, i.e., the white and red blood cells, are removed from the fluid. In one preferred embodiment, the cancer cells having different densities are prostate cancer cells.

Any fluid containing rare and non-rare cells can be processed according to the invention. Embodiments of the invention are suitable for enriching rare cells in a fluid wherein the ratio of rare cells to non-rare cells in the fluid is at least about 1:10,000, and are especially suitable for enriching rare cells in a fluid wherein the ratio of rare cells to non-rare cells in the fluid is at least about 1:100,000. In accordance with the invention, the concentration of rare cells can be increased by at least about 10-fold, preferably, increased by at least about 100-fold, and in some embodiments, increased by at least about 500-fold, as compared to the ratio of rare cells to non-rare cells in the original sample.

The present invention, particularly for some of those embodiments wherein the rare cells to be enriched are cancer cells, is capable of providing relatively high levels of cancer cell recovery from fluids. For example, recoveries as high as 70%, or more, based on the number of cancer cells in a blood sample have been observed. In addition, some embodiments provide sufficiently highly sensitivity to allow one to detect at least 1.5 cancer cells per milliliter of blood (e.g., from a 20 ml blood sample).

The method of the present invention is surprising and unexpected in that it can provide the foregoing advantages while utilizing "negative selection", i.e., binding the non-rare cells, a procedure that is precisely the opposite of conventional processes, that utilize "positive selection", i.e., binding the rare cells.

Examples of fluids that can be processed in accordance with the invention include bodily fluids, e.g., blood, urine, saliva, lymph, spinal fluid, semen, amniotic fluid, cavity fluids, and tissue extracts.

The rare cells that can be enriched in accordance with the invention include a variety of cells of therapeutic or diagnostic interest, including but not limited to, cancer cells. In those embodiments wherein the fluid to be processed comprises a bodily fluid, the rare cells are cells that are present in, or produced by, the body, and are not normally present in the bodily fluid. For example, the rare cells in the fluid can be cancer cells, and the non-rare cells can be non-cancer cells. In one embodiment, the rare cells are rare non-blood cells, such as, for example, prostate cancer cells.

The cancer cells, of course, can comprise a cell from any one of a number of different cancers including, but not limited to, those of epithelial origin. The term cancer should be further understood to encompass localized cancer (e.g., localized in tumors), as well as non-localized cancer. In particular, carcinomas of the bladder, brain, breast, colon, kidney, liver, lung, ovary, pancreas, prostrate, rectum, and stomach are included, as are tumors in the form of a sarcoma (e.g., a fibrosarcoma or rhabdosarcoma), a hematopoietic tumor of lymphoid or myeloid lineage, or another tumor, including, but not limited to, a melanoma, teratocarcinoma, neuroblastoma, or glioma.

In accordance with the invention, fluids comprising rare and non-rare cells are subjected to density gradient separation before carrying out negative selection. This is advantageous, particularly for those embodiments wherein the rare cells are cancer cells, since in general (using a bodily fluid such as blood for example), the density of most cancer cells is less than other circulating blood cells, such as nucleated white blood cells, due to the fact that such cancer cells are much larger, and thus lighter per unit mass, than the other blood cells. This being said, however, some cancer cells are heterogenous in nature, and certain kinds of cancer cells can have densities that are similar to that of nucleated white blood cells. Accordingly, as will be described in more detail below, some embodiments of the invention include carrying out density gradient separation at least twice, and/or using one or more multiple density gradient columns (i.e., columns having two or more density gradients) to further improve the efficiency of the enrichment process.

Density Gradient Separation

Generally, density gradient separation processes involve preparing one or more layers of gradient media, wherein the density or densities of the gradient media should be higher than the density of the rare cells to be separated. Typically, the fluid comprising rare cells and non-rare cells is placed onto the upper layer of the gradient medium (or uppermost gradient medium), the media and the fluid are centrifuged until the components of the fluid separate from one another according to their individual component densities.

For example, using FIG. 1 for reference, and using a bodily fluid such as blood as an illustrative fluid comprising rare cells and non-rare cells, the contents of the centrifuge tube can appear after centrifugation as follows: a plasma layer (Plasma I), an interface layer (Interface I), a density gradient layer (Gradient I), and a cell pellet (Pellet I) which resides at the bottom of the tube. The interface layer is flanked by the plasma layer on one side, and the density gradient layer on the other.

Rare cells that exist in both relatively light and heavy forms (e.g., some cancer cells such as prostate cancer cells), will be present in the interface layer, the adjacent density gradient layer, and in the cell pellet. Typically, the lighter cancer cells will be located in the interface layer and in the gradient layer, while the relatively heavier cancer cells will be located in the cell pellet along with the white and red blood cells.

In accordance with embodiments of the invention, one can prepare a first fluid suspension comprising an increased concentration of the "lighter" rare cells, and a second fluid suspension comprising an increased concentration of the "heavier" rare cells. This can be advantageous, since the rare cells having different characteristics can be processed differently according to the invention to improve rare cell recovery and reduce the presence of non-rare cells, while minimizing stress to the more fragile rare cells. Illustratively, the suspension comprising an increased concentration of heavier rare cells can be exposed to an agent that binds the non-rare cells, and the bound non-rare cells can be removed. However, the suspension comprising an increased concentration of the lighter rare cells (that may be larger, more fragile and/or sticky) need not be exposed to the binding agent.

For example, again using FIG. 1 for reference, a first fluid suspension comprising an increased concentration of lighter rare cells can be prepared by removing the interface layer (Interface I) and, preferably, the portion of the density gradient layer (Gradient I) adjoining the interface layer, and placing the interface layer and the gradient layer in another tube. Care should be exercised in removing the gradient layer so as not to disturb the cell pellet (Pellet I). Typically, about two-thirds of the adjoining gradient layer is removed.

Figure 5:
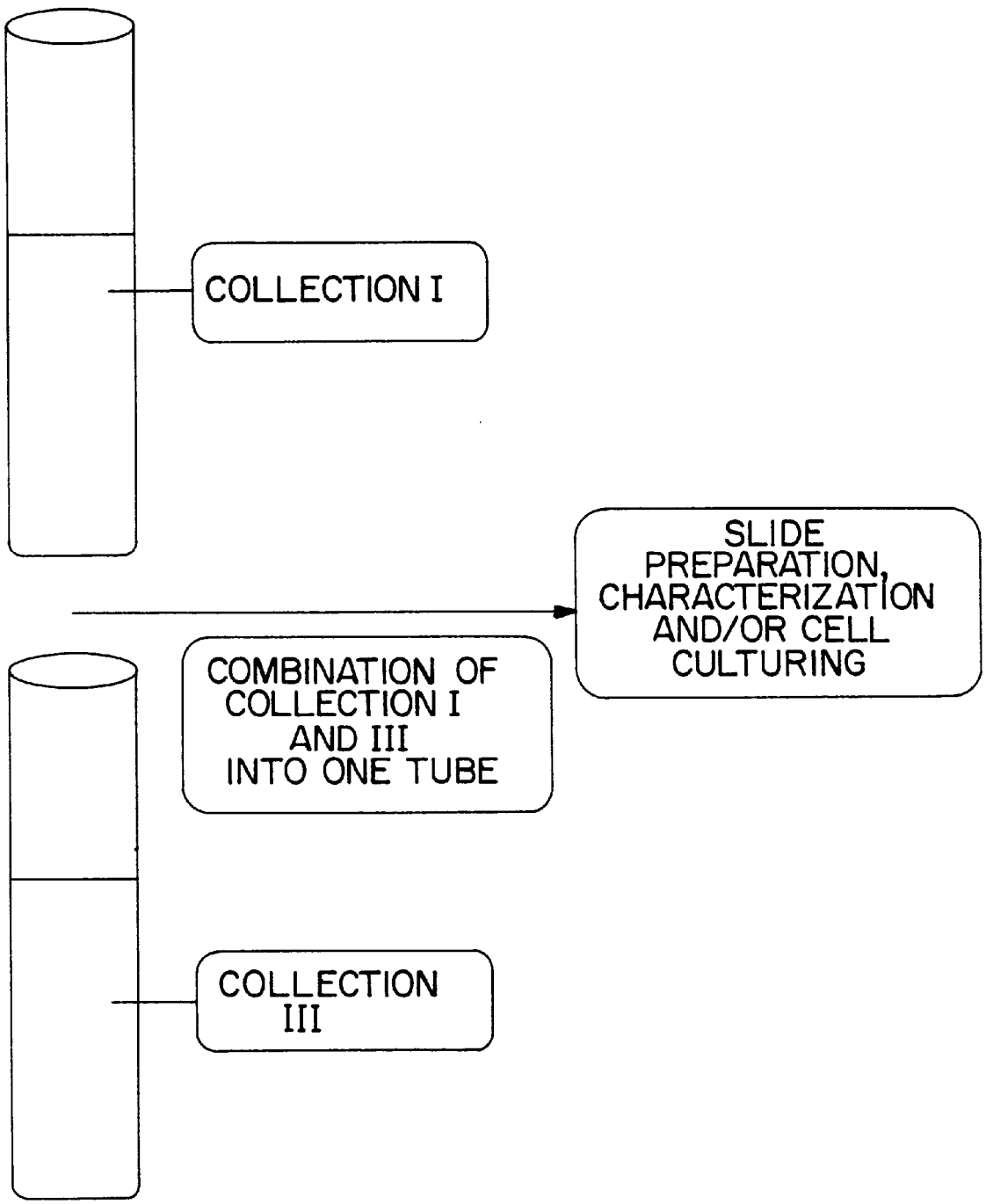
FIG. 5 schematically depicts that the Collection I and III fluids, that each include rare cells, can be combined. If desired, the rare cells can be used for cell culturing and/or slide preparation.

Thereafter, the cells in the new tube are gently washed with a suitable diluent, such as phosphate buffered saline (PBS), and are then lightly centrifuged (e.g., centrifuged at a force of about 200×g). The cell pellet that results from this processing is then suspended in a solution to form a first fluid comprising an increased concentration of rare cells, illustrated as the "Collection I" fluid in FIGS. 1 and 5. Suitable solutions for use in forming the Collection I fluid include, for example, an albumin solution, such as a 1 wt. % bovine serum albumin solution. The resulting cell suspension (the Collection I fluid), in which the relatively light cancer cells predominate, can be used for a variety of purposes, e.g., cell identification, and/or culturing, as will be discussed in greater detail herein. If desired, this fluid can be subjected to a negative selection process to bind non-rare cells contained in the fluid, and the bound cells can be removed to produce a fluid enriched with rare cells.

In the case of rare cells such as cancer cells that are relatively heavy, or which comprise relatively light and heavy cells, a second fluid suspension comprising an increased concentration of rare cells (i.e., the relatively heavy cancer cells) can be prepared. For example, using FIGS. 1, 2A, and 2B for reference, the plasma layer (Plasma I in FIG. 1) and the cell pellet (Pellet I in FIG. 1), which were not used when the relatively light cells were enriched, are removed and combined in a new tube, as illustrated on the left in FIGS. 2A and 2B. This combination of the plasma and the pellet includes the relatively heavy cancer cells as well as red and white blood cells. Subsequently, this combination is subjected to a density gradient separation process. In some embodiments, prior to subjecting the combination to this separation process, the density of the combination is adjusted to correspond to approximate that of the original fluid sample. For example, in those embodiments wherein the original sample comprises blood, the density of the combination can be adjusted by adding plasma.

Figure 2A:
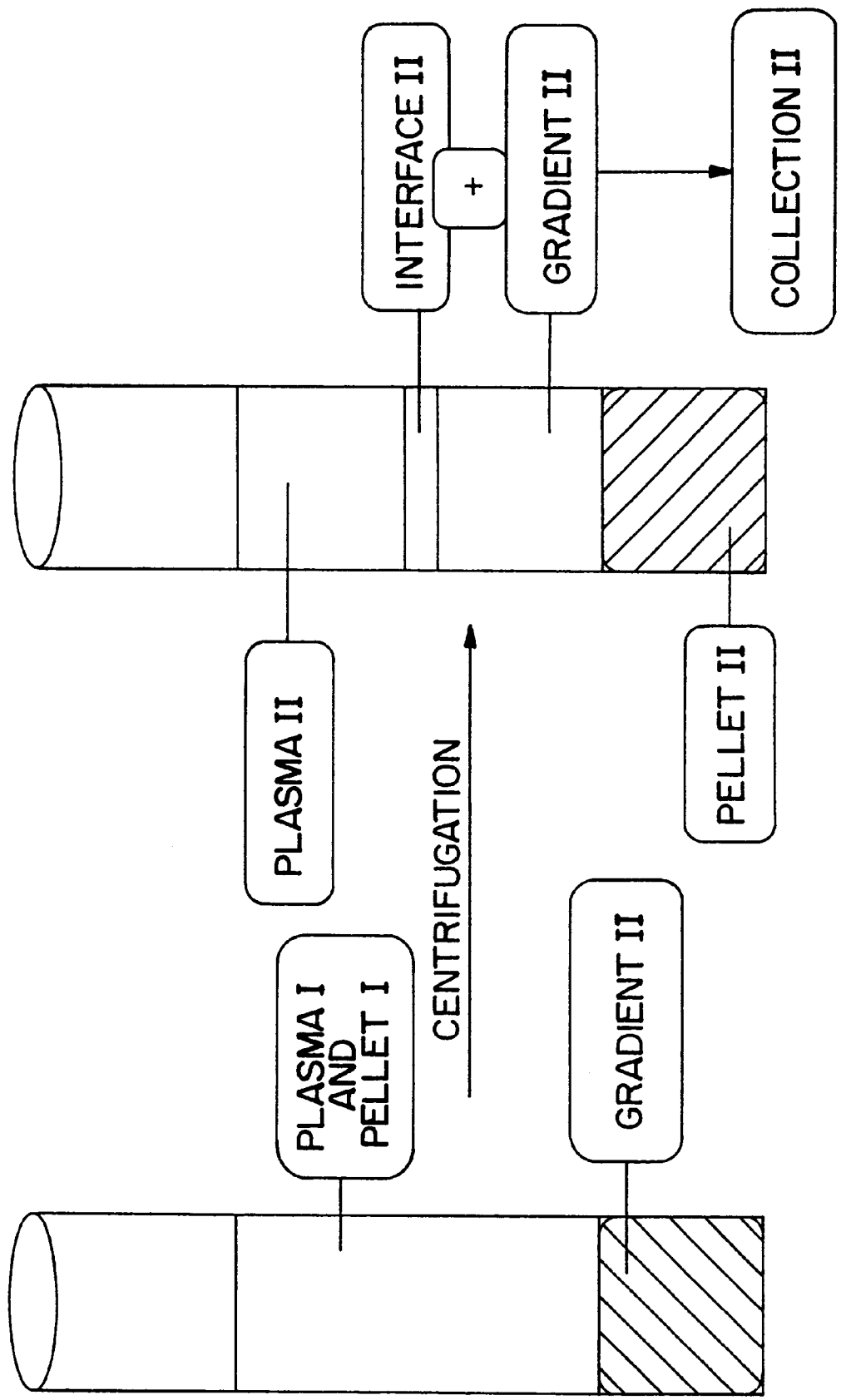
FIGS. 2A and 2B schematically depict centrifuging the combined Plasma I and Pellet I (from FIG. 1) on a single density gradient column (FIG. 2A) or a double density gradient column (FIG. 2B). The schematics illustrate the columns before (on the left) and after (on the right) centrifugation. Four regions are formed after centrifugation: Plasma II, Interface II, Gradient II, and Pellet II. Gradient II and Interface II will be combined to provide a second fluid including an increased concentration of rare cells, referred to below as the Collection II fluid.
Figure 2B:
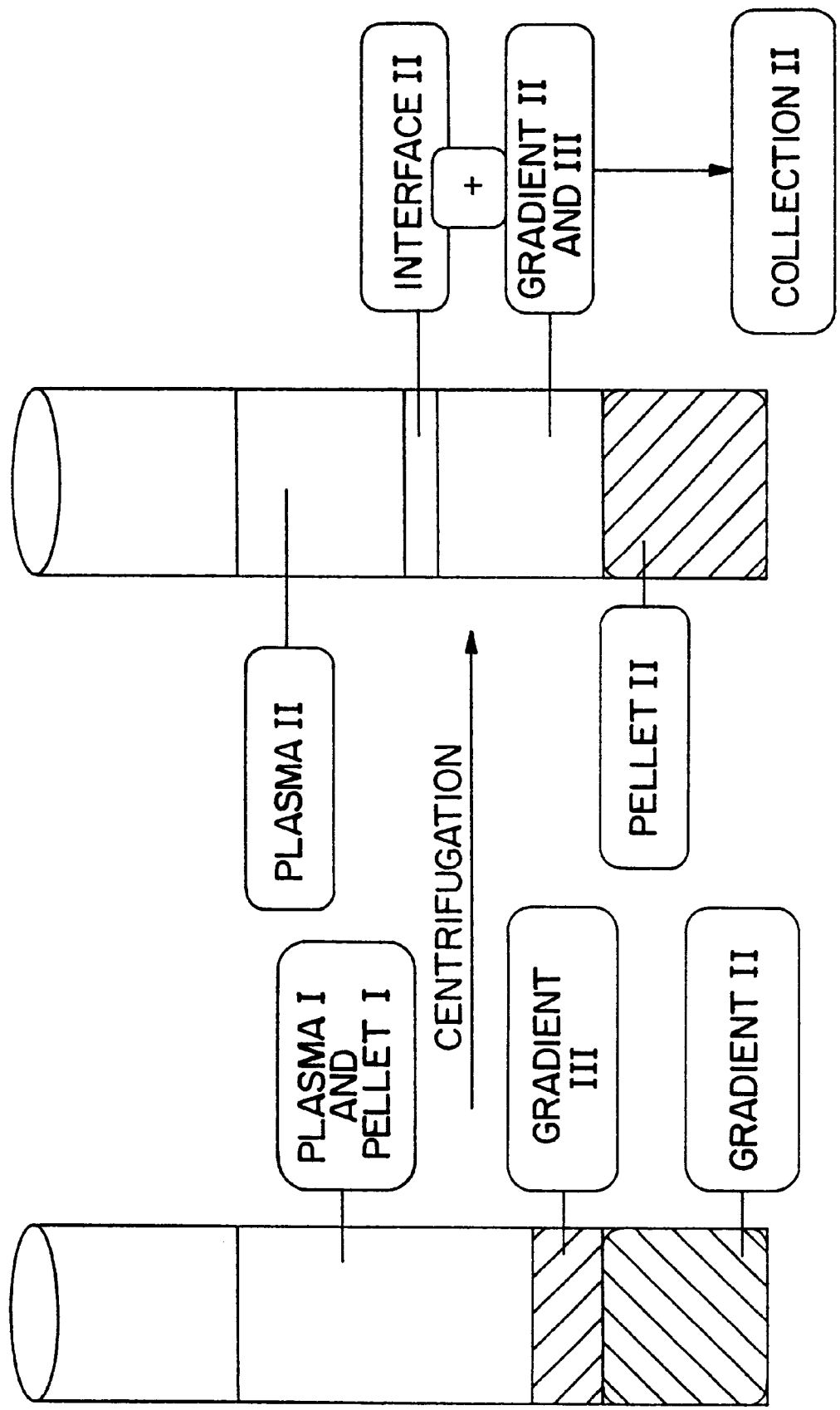

As a result of the separation process, the contents of the centrifuge tube can, as before, appear as four layers. For example, the right sides of FIGS. 2A and 2B illustrate a plasma layer (Plasma II); an interface layer (Interface II) containing the cancer cells as well as some white blood cells and red blood cells, a density gradient layer (Gradient II), and a cell pellet at the bottom (Pellet II).

Figure 4:
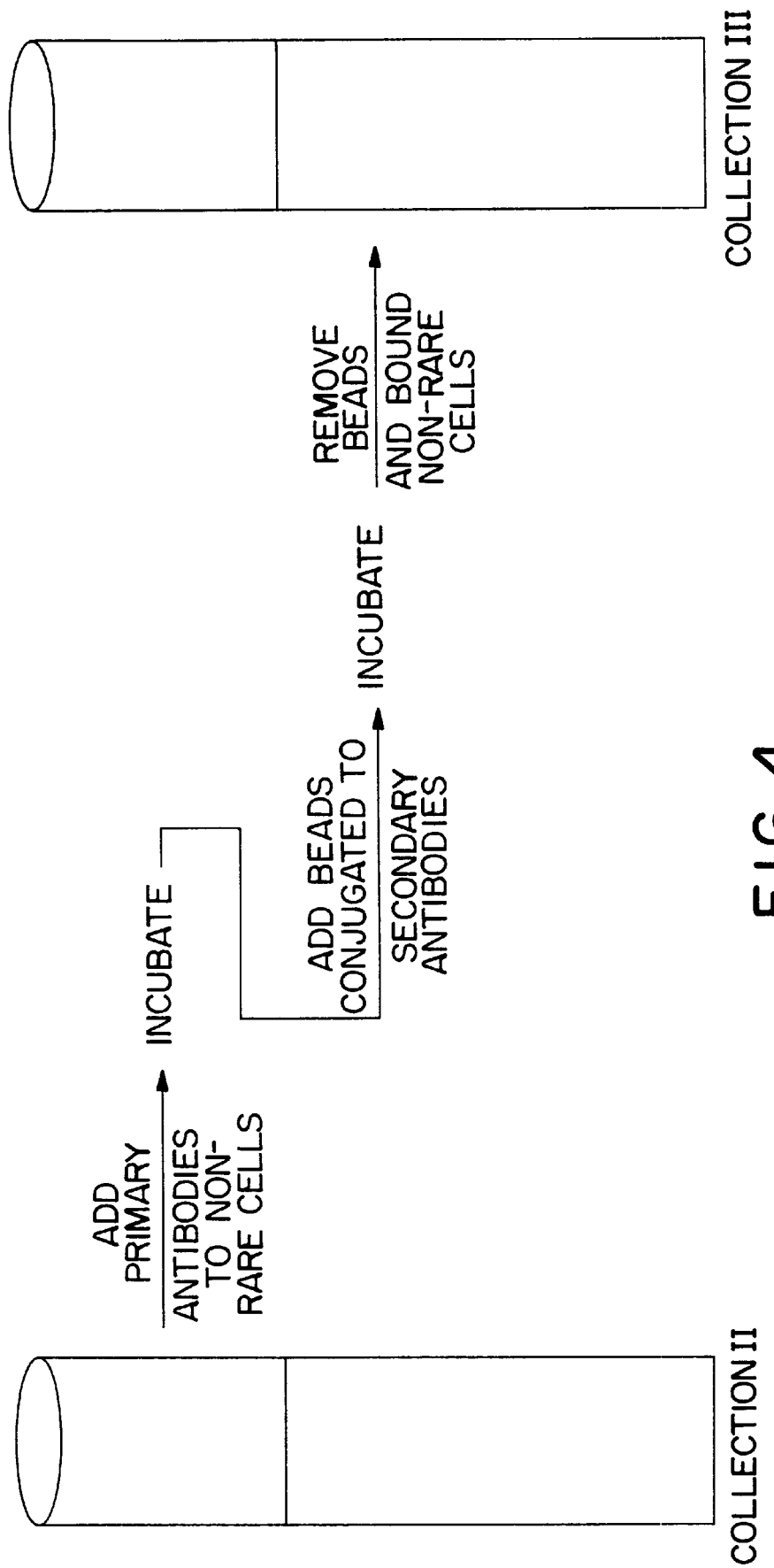
FIG. 4 schematically depicts one exemplary embodiment of the negative selection process of the present invention. The Collection II fluid is incubated with one or more primary antibodies to the non-rare cells, e.g., antibodies specific to white blood cell and/or red blood cell antigens. The Collection II fluid containing the primary antibodies is then incubated with secondary antibodies that are bound to supports such as magnetic beads. The primary antibodies bind to the non-rare cells, and the secondary antibodies (that are bound to the beads) bind to the primary antibodies. Accordingly, the removal of the beads from the fluid provides a fluid enriched with the rare cells, referred to below as the Collection III fluid.

The interface layer (Interface II) and, preferably, the portion of the density gradient layer (Gradient II) adjoining the interface layer, are removed and placed into a new tube. Thereafter, the cells in the new tube are gently washed with a suitable diluent, such as phosphate buffered saline (PBS), and, typically, are then lightly centrifuged. The cell pellet that results from this processing is then suspended in a solution to form a second fluid comprising an increased concentration of rare cells (as well as some white blood cells and red blood cells), illustrated as the "Collection II" fluid in the right side of FIGS. 2A, 2B, and in the left side in FIG. 4. Suitable solutions for use in forming the Collection II fluid include an albumin solution, such as a 1 wt. % bovine serum albumin solution. The resulting cell suspension (the Collection II fluid) is typically subjected to a negative selection process as will be described in more detail below in the section entitled "negative selection".

Figure 3:
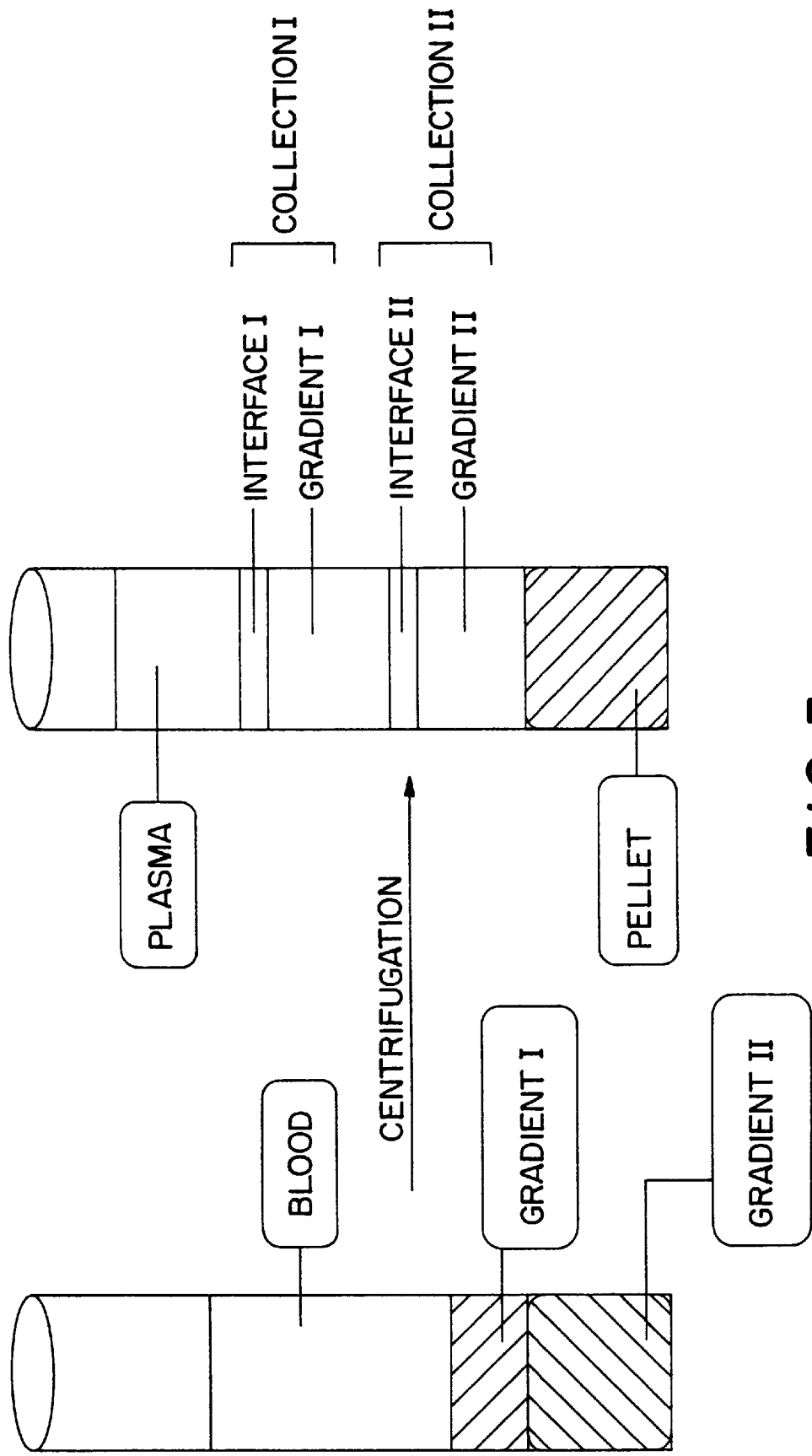
FIG. 3 schematically depict another embodiment of the invention, wherein a double density gradient column can be utilized to form six regions after centrifugation. The left side of FIG. 3 illustrates the double density gradient column and fluid sample (e.g., blood) before centrifugation, and the right side illustrates the column after centrifugation. Six regions are formed after centrifugation: Plasma, Interface I, Gradient I, Interface II, Gradient II, and Pellet. Interface I and Gradient I will be combined to form the Collection I fluid, and Interface II and Gradient II will be combined to form the Collection II fluid. The Collection I and II fluids each have an increased concentration of rare cells.

In an alternative embodiment, for example, as illustrated in FIG. 3, a multiple density gradient column can be utilized to provide a plurality of interface and gradient layers, and the appropriate layers can be combined and processed to provide one or more fluids having an increased concentration of rare cells.

For example, an embodiment of the gradient column as illustrated in FIG. 3 can be utilized to provide the Collection I fluid and the Collection II fluid, wherein each fluid has an increased concentration of rare cells. Illustratively, a bodily fluid such as blood can be placed on the upper layer of the gradient column, wherein the upper gradient density layer (Gradient I) has a density less than that of the lower layer (Gradient II). After centrifugation, the contents of the tube can appear as follows: a plasma layer (Plasma), a first interface layer (Interface I), a first density gradient layer (Gradient I), a second interface layer (Interface II), a second density gradient layer (Gradient II), and a cell pellet (Pellet) that resides at the bottom of the tube.

Typically, some of the lighter rare cells will be located in the Interface I and Gradient I layers, while some of the heavier rare cells will be located in the Interface II and Gradient II layers. In one embodiment (again using FIG. 3 for reference), the Interface I and Gradient I layers are combined to provide the Collection I fluid, and the Interface II and Gradient II layers are combined to provide the Collection II fluid. If desired, diluents can be used and/or suspensions can be formed as described above. The Collection I fluid and/or the Collection II fluid can be subjected to a negative selection process to bind the non-rare cells contained in the fluid(s), and the bound cells can be removed to produce fluid(s) enriched with rare cells.

A variety of density gradient media and protocols for carrying out density gradient separation are suitable for carrying out the invention. Thus, single and/or multiple density columns can be used, and any suitable combination of media densities can be employed. Of course, density gradient separation according to the invention can also be carried out using continuous and/or discontinuous gradients. Different media and protocols can be utilized depending on the fluid to be processed and the cells of interest. Density gradient separation can be carried out any number of times to provide one or more fluids having an increased concentration of rare cells. The gradient medium or media can also include one or more additives, e.g., to provide a desired density, or viscosity. Alternatively, or additionally, the additive(s) can provide for, for example, clumping and/or aggregating of non-rare cells during the density separation process.

In some embodiments, e.g., for separating relatively dense rare cells, such as, for example, dense prostate cancer cells, FICOLL 400™ is a preferred medium. The medium is generally used in combination with a compound, in solution, of relatively high density and relatively low viscosity, for example sodium metrizoate and sodium diatrizoate.

By way of example, and in some embodiments wherein the fluid comprises blood, density gradients containing cell aggregating or clumping agents such as methylcellulose, ISOPAQUE™, dextran, and FICOLL™ can be used. Bhat, N. M. J. Immuno. Meth., 158, 277–280 (1993). ISO-PAQUE™ is a sodium N-methyl-3,5,-diacetamino-2,4,6 -triiodobenzoate. FICOLL™ (Accurate Chemical and Scientific Corporation, Westbury N.Y.) is a synthetic high polymer made by the copolymerization of sucrose and epichlorohydrin. These agents cause erythrocyte clumping, and thus can be utilized to separate leukocytes from red blood cells.

PERCOLL™ (available from Pharmacia) density gradients are also suitable for the purposes of the present invention. PERCOLL™ is a colloidal polyvinyl pyrrolidone coated silica having a pH of 8.9±0.3 at 20° C., a density of 1.13±0.005 g/mL, and a viscosity of 10±5 cps at 20° C.

The following section describes using PERCOLL™ to provide a density gradient medium of any suitable density. It should be clear that other media and preparation protocols are also suitable, and can be readily determined by one of ordinary skill in the art. A stock solution of PERCOLL™ is prepared by combining the following ingredients: 90 mL of PERCOLL™, 9 mL of 10× Hank's Balanced Salt Solution (HBSS without calcium, magnesium, and phenol red), 1 mL of HEPES buffer (pH of 7.3), and 0.4 mL of 1 M HCl. The resulting solution has a pH of 7.4. Media having various illustrative densities can be obtained as follows. A medium having a density of 1.070 g/mL can be obtained by mixing 24 volumes of the PERCOLL™ stock solution and 20 volumes of 1× HBSS. A medium having a density of 1.079 g/mL can be obtained by mixing 27 volumes of the PERCOLL™ stock solution and 15.9 volumes of 1× HBSS. A medium having a density of 1.088 g/mL can be obtained by mixing 23 volumes of the PERCOLL™ stock solution and 10 volumes of 1× HBSS.

It may be advantageous to dilute the fluid comprising rare cells and non-rare cells with a suitable diluent prior to placing it on the density gradient column, particularly for those embodiments wherein the fluid comprises blood. Any suitable diluent known to those of ordinary skill in the art can be employed. Examples of such diluents include buffers, e.g., physiological buffers such as Tris buffer, phosphate buffer, citrate buffer, and phosphate buffered saline (PBS), and salt solutions, e.g., commercially available balanced salt solutions such as Hanks balanced salt solution (HBSS), Earl's balanced salt solution, Gey's balanced salt solution, and the like. PBS is a preferred diluent for diluting blood.

The fluid can be diluted with the aforesaid diluent to any desired ratio. Typically, however, in those embodiments wherein the fluid is a blood sample, it is diluted in a volume ratio of from about 0.1 to about 10 (blood:diluent), advantageously in a volume ratio of from about 0.5 to about 5 (blood:diluent), and preferably in a volume ratio of from about 1 to about 2 (blood:diluent).

After the fluid sample is placed on the column, the column and the sample are centrifuged. Centrifugation will typically be performed in any suitable centrifuge, and at a suitable force and for a suitable length of time, so that the lighter rare cells are separated from the heavier non-rare cells and other material. In some embodiments, the force of centrifuging should generally range from a force of from about 300×g to about 600×g, preferably, from about 350×g to about 450×g. Of course, in other embodiments, the centrifuge can operate at a higher force, or a lower force, than described above.

Centrifugation can be carried out to any suitable length of time. In some embodiments, centrifugation is carried out for about 1 minute to about 60 minutes, advantageously for about 10 minutes to about 50 minutes, and preferably for about 20 minutes to about 40 minutes. In the case where blood is the fluid being processed, the centrifuging is preferably carried out for a period of about 30 minutes at a force of about 400×g.

Although those skilled in the art will be able to determine the appropriate densities, in the specific case of enriching prostate cancer cells in blood, the gradient medium (gel) should have a density of no less than about 1.06 g/mL, more preferably no less than about 1.068 g/mL. In one embodiment involving the enrichment of prostate cancer cells, and utilizing a double density gradient, the double gradient should include layers having a density ranging from about 1.06 g/ml to about 1.10 g/ml, with about 1.077 g/ml to about 1.083 g/ml being preferred.

Embodiment of the method of the present invention encompass the enrichment of many types of cancer cells that can circulate in a fluid such as blood. For example, as described below, cells from the classical Hepatoma $G_2$ cell lines were cultured and put into normal human blood in known numbers. These samples were centrifuged in various density gradients. The density gradient having a density of 1.068 g/mL was found to be the gradient layer from which 80% of added hepatoma cells were recovered. The hepatoma cells also were found to be very sticky and fragile. It is believed that these hepatoma cells have a similar density to the prostate cancer cells of the LNCaP line.

Negative Selection

As noted earlier, the negative selection process comprises subjecting a fluid comprising rare cells and non-rare cells to an agent that binds non-rare cells, and removing the bound non-rare cells from the fluid. The removal of the bound non-rare cells provides a rare cell-enriched fluid.

For example, the Collection II fluid as described in any of the embodiments above can comprise the heavier rare cells, as well as some non-rare cells that may have similar densities (e.g., some white blood cells and red blood cells). Accordingly, the Collection II fluid can be subjected to an agent that binds these non-rare cells. The removal of the bound non-rare cells provides a rare cell-enriched fluid, represented as the "Collection III" fluid in FIG. 5.

In accordance with embodiments of the invention, the agent that binds to the non-rare cells typically comprises one or more antibodies, preferably monoclonal antibodies, that specifically bind to the non-rare cells. A variety of antibodies are suitable for carrying out the invention, and they can be derived from any suitable source. For example, in some embodiments, e.g., wherein the fluid comprising rare cells and non-rare cells includes blood cells, suitable binding agents include antibodies that specifically bind to one or more normal white blood cell surface antigens and/or red blood cell surface antigens. Alternatively, or additionally, the binding agent can comprise, for example, anti-human antibodies, e.g., that specifically bind to human normal white blood cells and/or human red blood cells.

The negative selection process encompasses both "direct" and "indirect" protocols. For example, one example of a direct negative selection process includes utilizing an antibody bound to a support wherein the antibody binds to a non-rare cell. An example of an indirect negative selection process includes using a "primary" antibody to bind to the non-rare cell, and a "secondary" antibody (that is bound to a support) to bind to the "primary" antibody. Preferably, the primary and secondary antibodies are from different species of animals. A variety of primary and secondary antibodies are suitable, and are commercially available.

The use of a support (e.g., a particle such as a bead, more preferably a microbead) is desirable, since it allows the antibody-non-rare cell combination or the secondary antibody-primary antibody-non-rare cell combination to be more readily removed from the fluid. Microbeads, which are well-known in the art, can be made of any suitable material, including plastic and magnetic materials, with magnetic microbeads being preferred, and superparamagnetic microbeads being even more preferred. A variety of suitable supports, particularly particles such as microbeads (with or without antibodies bound thereto) are commercially available. Any separation method and system known to those of ordinary skill in the art that is capable of removing the support (e.g., the particles) from the fluid can be utilized.

In one embodiment of a direct negative selection process, a fluid comprising an increased concentration of rare cells (e.g., the Collection II fluid), is contacted with a mixture of anti-human antibodies bound to support particles. The fluid thus produced is then incubated at a suitable temperature and for a suitable period of time so as to effect substantially complete binding of the antibodies to the non-rare cells. While the temperature and time of incubation will vary, the incubation is preferably carried out at a subambient temperature, and more preferably at about 4° C., for a period of from about 5 minutes to 60 minutes, and preferably for a period of from about 10 minutes to about 50 minutes.

During the incubation, the antibody/support particles and the cells are preferably gently mixed, e.g., by using a suitable mixing or shaking device. The support particles/ antibodies, that now have non-rare cells bound to the antibodies, are separated from the fluid as is known in the art. Illustratively, in some embodiments wherein the support particles are paramagnetic microbeads, the separation can be carried out using a magnetic particle concentrator. Suitable concentrators are commercially available, e.g., from Dynal, Inc. (Lake Success, N.Y.).

In an embodiment of an indirect negative selection process, a fluid comprising an increased concentration of rare cells (e.g., the Collection II fluid), is contacted with a mixture of primary antibodies, e.g., anti-human antibodies. These primary antibodies are not bound to supports. The resulting mixture can then incubated as described above for the direct method. Thereafter, the fluid is contacted with secondary antibodies which are bound to support particles. These secondary antibodies are selected so as to be specific to the primary antibodies. The support particles/secondary antibodies, that now also have primary antibodies/non-rare cells bound thereto, can be separated from the fluid as described above with respect to the direct negative selection process, e.g., by using a magnetic particle concentrator.

As noted above, in some embodiments, the use of superparamagnetic particles is preferred. Exemplary superparamagnetic microbeads have a magnetic susceptibility of from about $10^{-9}$ cgs units to about $10^{-7}$ cgs units, and preferably from about $8 \times 10^{-9}$ cgs units to about $10^{-7}$ cgs units. One embodiment involving the use of a magnetic particle concentrator to separate the paramagnetic (or superparamagnetic) particles from the fluid can be described as follows. When the fluid is placed within the magnetic field generated by magnetic particle concentrator, the paramagnetic particles are attracted to and held close to the wall of the tube in proximity to the magnet of the magnetic particle concentrator, providing for the separation of the non-rare cells (bound to the paramagnetic particles) from the rare cells (that are unbound). The rare cells enriched according to this embodiment are substantially free of contamination by non-rare cells. For example, in the case of the separation of cancer cells from blood, it was found that the cancer cells could be almost completely separated from nucleated white blood cells. This can be advantageous because nucleated white blood cells, if present, can interfere with cell identification, particularly for some of the embodiments wherein polymerase chain reaction (PCR) methods are used.

For some of the embodiments wherein the fluid comprising rare cells and non-rare cells is blood, it may be desirable to use antibodies that bind to white blood cells (leukocytes) and/or red blood cells (erythrocytes). Examples of suitable leukocyte antibodies include the human and anti-human leukocyte CD antibodies, e.g., CD2, CD3, CD4, CD5, CD7, CD8, CD11a, CD11b, CD11c, CD14, CD15, CD16, CD19, CD20, CD28, CD36, CD42a, CD43, CD44, CD45, CD45R, CD45RA, CD45RB, CD45RO, CD57, and CD61 antibodies, and the like. Antibodies targeted to human CD45, CD3, CD19, CD14, and CD36 are preferred. For example, when an CD45 specific antibody is used, it recognizes the CD45 leukocyte common antigen (LCA) family which is comprised of at least four isoforms of membrane glycoproteins (220, 205, 190, 180 kD) present on cells of the leukocyte lineage. Of course, human and anti-human red blood cell antibodies can also be included.

By way of example of a direct negative separation embodiment, the rare cell-containing fluid can be contacted with a mixture of anti-human CD45, anti-human CD19, anti-human CD14, and anti-human CD3 antibodies (e.g., a mixture of mouse anti-human CD45 IgG, mouse anti-human CD19 IgG, mouse anti-human CD14 IgG, and mouse anti-human CD3 IgG antibodies). Optionally, a suitable anti-human red blood cell antibody (e.g., glycophorin A) can also be included in the antibody mixture. In one embodiment, the antibodies are bound to magnetic particles before exposing the mixture to the rare cell-containing fluid, and the particles are removed from the fluid using a magnetic particle concentrator as described above.

By way of example of an indirect negative separation embodiment, where a mouse anti-human CD45 IgG antibody is used as the primary antibody, the secondary antibody would be anti-mouse IgG antibody. The secondary antibodies can be bound to particles before use, and removed from the rare cell-containing fluid, as described above.

In accordance with an embodiment of the invention, a kit for the enrichment of cancer cells from blood is provided, comprising at least first and second gradient density media, wherein the first gradient density medium has a density of at least about 1.067 g/mL, and the second gradient density medium has a density of at least about 1.077 g/mL, wherein the kit further comprises support particles, and at least one antibody capable of binding to a cell surface antigen of a cell that is more dense than the cancer cell. In a more preferred embodiment, the first gradient density medium has a density of about 1.068 g/mL to about 1.077 g/mL, and the second medium has a density of from about 1.077 g/mL to about 1.085 g/mL.

In other embodiments of kits according to the invention, the kit can include one or more nucleic acid probes (described below in the section entitled "Further Processing of the Enriched Rare Cells") and/or one or more antibodies. If desired, such kits can also include one or more gradient density media.

Further Processing of the Enriched Rare Cells

As noted earlier, a fluid comprising rare cells and non-rare cells can be processed to provide a plurality of fluids, each having an increased concentration of rare cells. One or more of the fluids having an increased concentration of rare cells can be subjected to a binding agent to bind the non-rare cells, to provide one or more rare cell-enriched fluids. If desired, the fluids can be combined. For example, two rare cell-enriched fluids can be combined, or a rare cell-enriched fluid can be combined with a fluid that has an increased concentration of rare cells, but was not subjected to a binding agent.

Embodiments of the invention provide one or more rare blood cell enriched fluids that are suitable for a variety of purposes.

Embodiments of the method according to the present invention also provide for processing or using the enriched rare cells, e.g., to identify, characterize, and/or culture the rare cells. Additionally, the method provides for diagnosing cancer, particularly prostate cancer in men, and also allows monitoring the progress, or regression, of cancer, particularly during or after therapy.

The present invention further provides a method of identifying cancer cells in a patient's blood comprising enriching the cancer cells from the patient's blood by any of the methods set forth above, and identifying the cells using any suitable protocol and system.

Embodiments of the present invention also provide for preparing a therapeutic product, including, but not limited to, a vaccine.

The cells can be prepared (e.g., for identification, characterization, and/or culturing) by any suitable procedure. Typically, an embodiment of the method for identifying and/or characterizing the rare cells includes preparing a suspension including the enriched cells, transferring the suspension of cells to a microscope slide (e.g., to prepare a smear), and examining the smear using a light microscope. In the direct smear procedure, it is preferred to avoid packing the cancer cells down through a centrifugal force or redistributing these packed cells by mechanical means.

On the other hand, if the cells are gently sedimented or centrifuged down, and after the supernatant is carefully removed, the loosely sedimented cells can be resuspended by a small volume of liquid (about 1–10 $\mu$l), and then be directly transferred onto a slide (e.g., for identification) or onto a growth medium (e.g., for culturing). One protocol for transferring the cells onto a slide includes resuspending the sedimented cells in BSA solution, and cytospinning the cells onto the slide, e.g., by using a commercially available Megafunnel™ large volume sample chamber (Shandon).

If desired, the sedimented cells can be fixed by addition of a fixative (such as ethanol), thus rendering the cells more damage-resistant. This can be advantageous, as the fixed cells can be readily transferred to the slide. However, since the cells are fixed, they cannot be cultured or used for PCR studies.

If desired, a machine collection procedure for preparing cells for identification can avoid exposing the cells to the stresses of centrifugation. For example, the few cancer cells in solution can be advantageously collected from the suspension and deposited on a membrane while creating gentle suction. The liquid will pass through the pores of the membrane, and the cells will be collected on the membrane. These cells are then transferred to the slide by putting the cell-containing surface of the membrane onto the slide.

A variety of techniques are suitable for identifying and/or characterizing the rare cells. Additionally, embodiments of the invention can include identifying and/or characterizing a plurality of types of rare cells, e.g., different cancer cell types, in a single sample. Suitable techniques include, for example, immunocytochemical staining with monoclonal antibodies, nucleic acid hybridization (including in situ hybridization) and polymerase chain reaction (PCR) studies. The technique can include utilizing a "cocktail" of antibodies and/or probes.

Illustratively, in some embodiments wherein the rare cells are cells of epithelial origin, e.g., prostate cancer cells, they can be identified by immunocytochemically staining them with monoclonal antibodies that specifically bind to, for example, PSA (prostate specific antigen), PSMA (prostate specific membrane antigen), PSAP (prostate specific acid phosphatase), cytokeratin protein, or albumin. Although PSA is widely used for identification of prostatic cells' activities, there are certain prostate cells which secrete little or no PSA. Therefore, in some embodiments it may be desirable to alternatively, or additionally, use antibodies that specifically bind to PSMA.

Of course, rare cells can also be identified and/or characterized using nucleic acid hybridization protocols. For example, in some embodiments wherein the rare cell is a liver cancer cell, suitable nucleic acid probes include oligomeric probes that specifically bind to serum albumin mRNA and $\alpha$-fetoprotein mRNA, for example. Alternatively, in some embodiments wherein the rare cell is a prostate cancer cell, suitable probes include those specific for, for example, PSA, PSMA, chromosome 7, chromosome 8, and/or chromosome 18. As noted above, there are certain prostate cells which secrete little or no PSA. Thus, probing for PSA may be less sensitive than probing for PSMA.

Illustrative probes that are specific for mRNA encoding PSA, for mRNA encoding PSMA, and for the centromeric regions of chromosomes 7, 8, and/or 18, are described in more detail below. These probes are particularly suitable for in situ hybridization.

Representative probes that are specific for PSMA (prostate specific membrane antigen) mRNA include:

SEQ. ID. No. 1: TGGCTGTGCG CTGGGGCGCT GGT-GCTGGCG GGTGGCTTCT TTCTCCTCGG CTTC-CTCTTC GGGTGGTTTA TA,

SEQ. ID. No. 2: AGTGTCTATG AAACATATGA GTTG-GTGGAA AAGTTTTATG ATCCAATGTT, and

SEQ ID. No. 6: GTGTTTGAGC TAGCCAATTC CAT-AGTGCTC CCTTTTGATT GTCGAGATTA.

Representative probes that are specific for PSA (prostate specific antigen) mRNA include:

SEQ ID. No. 3: GGTCCTCACA GCTGCCCACT GCAT-CAGGAA CAAAAGCGTG ATCTTGCTGG GTCGGCACAG,

SEQ ID. No. 4: CGCTGGACAG GGGGCAAAAG CACCTGCTCG GGTGATTCTG GGGGCCCACT TGTCTGTAAT,

SEQ ID. No. 7: TCTTCCTCAC CCTGTCCGTG ACGTGGATTG GTGCTGCACC CCTCATCCTG TCTCGGATTG, and SEQ ID. No. 8: CAGGCTGGGG CAGCATTGAA CCA-GAGGAGT TCTTGACCCC AAAGAAACTT CAGTGT-GTGG.

Representative probes that are specific for the repetitive sequences in centromeric regions of chromosomes 7, 8 and 18 include:

SEQ ID. No. 5: GCTGTGGCAT TTTCAGGTGG AGATTTCAAG CGATTTGAGG ACAATTGCAG (chromosome 7).

The probes for the centromeres can be used to determine the number of chromosomes in the cells, e.g., to determine aneuploidy. For example the probes for the centromere of chromosome 7 can be used to count the number of chromosome 7's in the cell. The normal cell should be diploid, and thus exhibit two stained probe "dots". Deviation from the diploid state (i.e., 1, 3, 4 or a greater number of chromosome 7's) would indicate aneuploidy or an abnormal number of chromosomes which is a very strong indication of a cancerous/neoplastic state.

A suitable probe for the chromosome 8 centromere can be obtained commercially, for example, from Vysis, Inc. (Downers Grove, Ill.).

A suitable probe for the chromosome 18 centromere is SEQ ID. No. 9: GTACTCACAC TAAGAGAATT GAAC-CACCGT. Meyne et al. in *Methods in Molecular Biology, 33. In Situ Hybridization Protocols*, Choo, H. K. (ed.), 63–74 (1994). This sequence can be converted to a longer sequence. For example, it can be converted to SEQ. ID No. 10: ATGTGTGTAC TCACACTAAG AGAATTGAAC CACCGTTTTG AA. Although a sequence length of about 20 to about 60 nucleotides can be used, a preferred length is 42.

Of course, rare cells can also be identified by polymerase chain reaction (PCR) techniques. Any PCR technique and suitable probe(s) known to those of ordinary skill in the art can be employed.

The present invention further provides a method of identifying cancer cells in a patient's blood comprising enriching the cancer cells from the patient's blood by any of the methods set forth above, and subjecting the cells to in situ hybridization, including Fluorescent In Situ Hybridization (FISH). Suitable probes include those described above. Additionally, exemplary in situ hybridization protocols and probes used therein can be found in, for example, Meyne et al. in *Methods in Molecular Biology*, Vol. 33, as referenced above.

Illustratively, the FISH probes can be synthesized with deoxyribose nucleotidyl units, or 2'-O-methylribosyl nucleotidyl units, or the nonionic analogs consisting of methyphosphonate backbone or phosphorothiolate nucleotidyl backbone. Suitable probes include oligodeoxyribonucleotide probes, and preferably those labelled with a fluorescent residue. Any suitable fluorescent residue can be employed. Thus, fluorescent dyes such as fluorescein (green), cy3 (red), cy5 (far red), cy7 (infrared), and Texas red can be the labels. Dual and triple in situ hybridization also can be carried out by using a combination of mRNA and centromere probes (differentially labeled) under the conditions described above. After a high stringency wash, the nuclei of the cells can be counterstained with a fluorescent DNA stain such as DAPI (diamidino phenylindole) or PI (propidium iodide). The stained cells can be analyzed for specific mRNA and aneuploidy using any suitable fluorescence microscope. Suitable systems and protocols including the use of a fluorescent microscope include those described in, for example, Callahan, et al. *Cytometry* 13, 453–461 (1992), and Lesko et al. *Exp. Cell Res.* 219, 499–506 (1995).

One alternate procedure for assaying aneuploidy in cancer cell nuclei is to first conduct specific immunocytochemical staining (for example, by staining PSA, PSMA, PSAP, or albumin) and crosslinking the antibodies and antigens, followed by in situ hybridization with fluorescently labelled centromere probes.

One procedure for detecting epithelioid cancer cells includes specific immunocytochemical staining (e.g., by cytokeratonal protein antibodies that specifically bind to cytokeratin protein expressed by the cells), then postfixation and/or crosslinking the antibodies and antigens, followed by in situ hybridization for the detection of specific mRNA and chromosome aneuploidy.

In order to carry out FISH, the slides should be cleaned prior to placing the cells on them, by immersing in a dilute hydrochloric acid solution, e.g., 0.1 N HCl, at room temperature for about 20 minutes for denaturation of any DNA and RNA residues. The HCl solution should contain 0.1% Triton X100 surfactant. The slides are then rinsed with PBS.

The rare cells, e.g., cancer cells, can be loaded on the slides by any suitable procedure as previously discussed. The slides are then dehydrated by immersing sequentially in 75% ethanol, 85% ethanol, and 95% ethanol, for a period of about 2 minutes for each ethanol immersion.

An exemplary FISH cocktail includes 200 ng of each PSMA and PSA probes as well as 250 ng of chromosome 7 centromere probe, 10 μl of in situ hybridization buffer (25% formamide 4×SSC for oligomere probes, and 50% formamide and 1×SSC for commercial probes) are added to the slide. The cells are then covered with a cover slip, and the edges of the slide are surrounded by rubber cement and sealed. The slide should be kept in the oven (e.g., at 80° C. for about 5 minutes) for denaturation and then incubated, e.g., at 42° C. for about 3 hours. The cells are then washed, e.g., with 1×SSC, 65° C. for about 10 minutes. The cells are subsequently stained by a suitable dye, such as, for example, diamidino phenylindole (DAPI), and then examined under a suitable microscope.

Embodiments of the present invention further include culturing rare cells. For example, rare cells such as cancer cells can be enriched as described above, and subsequently placed in contact with a suitable growth medium. Typically, in order to carry out culturing the cells, the cells are loaded onto a sterile membrane filter.

Any suitable membrane filter known to those of ordinary skill in the art can be employed. Examples of suitable membranes include microporous membranes. The membranes can have any suitable pore size, preferably a pore size of from about 0.2 μm to about 15 μm, and more preferably 15 μm. Examples of suitable microporous membranes include nylon 6, nylon 46, nylon 66, and nitrocellulose membranes. Suitable membranes are commercially available.

The cells are not "fixed" prior to loading onto the membrane. The membrane with the cells loaded onto it is then typically placed in a collagen coated petri dish containing a growth medium with the cells being in contact with the collagen coated surface. Any suitable growth medium known to those of ordinary skill in the art can be employed. An example of a growth medium is PFMR-4A supplemented with 1% serum and additional factors (Peehl, *J. of Tissue Culture Methods*, 9, 53–60 (1985)). Examples of other suitable growth media include RPMI 1640, Coon's F12, Dulbecco's Modified Eagle Medium, McCoy's Medium, and the like.

The cell growth can be monitored by a suitable method known to those of ordinary skill in the art. For example, prostate cancer cell growth can be monitored by analyzing for PSA secretion into the culture medium with an Enzyme Linked Immunosorbent Assay (ELISA), and liver cell growth can be monitored with an ELISA by assaying the secretion of albumin or α-fetoprotein.

The cultured cells have a variety of additional uses. For example, the cells can be used to provide a therapeutic product, including, but not limited to, a vaccine.

The present invention further provides a method of diagnosing cancer, particularly prostate cancer in men, the method comprising enriching and identifying the cancer cells from the blood of the patient as described above The present invention further provides an improved method of staging cancer in human beings, particularly a method of staging prostatic cancer in men. For example, in one embodiment, the blood of a suspected cancer patient is processed as described above to enrich the prostate cancer cells (if present). An enhanced reverse transcriptase (RT) polymerase chain reaction (PCR) assay utilizing oligonucleotide primers is then carried out. Since the present inventive method is highly efficient in enriching cells and embodiments are capable of detecting 1 cancer cell in 6 million cells, the method of the present invention is significantly more sensitive than the methods reported in the literature, which are said to be capable of detecting one PSA-producing cell in 100,000 lymphocytes (Katz et al., *Urology,* 43, 765–775 (1994)) and 1 in 1 million cells (Israeli et al., *Cancer Research,* 54, 6306–6310 (1994)). In addition, the present method identifies PSA-synthesizing cancer cells, as well as non-PSA-synthesizing cancer cells, such as PSMA-synthesizing cells.

The present invention further provides a method of monitoring the progress, or regression, of cancer during or after therapy, and finds particular use with respect to prostate cancer in men. The method comprises taking repeated blood samples over time and enriching, isolating, and subsequently identifying the cancer cells (if present) from the blood of a patient suspected of having cancer as described above. Embodiment of the present invention, in view of their enhanced sensitivity, are particularly useful in monitoring the efficacy of various cancer treatments by isolating and detecting cancer cells in the patient's blood stream.

The following examples further illustrate the present invention but, of course, should not be construed as in any way limiting its scope. In all of the following examples, the enriched cells are identified using an automated Zeiss Axiovert 35 epifluorescent microscope equipped with a cooled charge coupled device (CCD) camera and filter cubes which will allow additional differential detection of fluorescein cy3, cy5, and cy7 fluorescent signals. The camera has a computer controlled shutter. The computer also controls the movement of the slide stage of the microscope.

The microscope is put in automated mode and multiple wavelength exposures are taken. The images are downloaded to the computer via an A to D converter. The computer processes and records the images in digital form.

EXAMPLE 1

This example illustrates the density measurements of prostatic cancer cells and hepatoma cells, e.g., to improve the efficiency in selecting suitable density gradient media for the practice of the present invention. The density of the cancer cells is measured in a density gradient column by determining the percent recovery of the cancer cells at the interface of the culture medium and the gradient medium.

A stock solution of PERCOLL™ (Sigma Chemical Co., St. Louis, Mo.) is prepared by adding 9 parts of PERCOLL™ to 1 part (V/V) of 1.5 M NaCl solution. The osmolality of the PERCOLL™ solution is adjusted with physiological saline. Final adjustment to the required osmolality can be made by adding distilled water or salts. The density of the stock PERCOLL™ solution can be calculated from the following formulas:

$$Vx = Vo \frac{(Po - P1)}{(P1 - P10)} \qquad P1 = \frac{(VoPo + VxP10)}{Vx + Vo}$$

wherein
  Vx=Volume of diluting medium (ml)
  Vo=Volume of PERCOLL™ (ml)
  Po=density of PERCOLL™ (1.130±0.005 g/ml)
  P10=density of 1.5 M NaCl=1.058 g/ml of 2.5 M sucrose=1.316 g/ml
  P1=density of stock solution produced (g/ml)

Thus, for stock PERCOLL™ in saline P1=1.123 g/ml, and for stock PERCOLL™ in sucrose P1=1.149 g/ml.

Solutions of stock PERCOLL™ can be diluted to lower densities by diluting with 0.15 M saline (density=1.008 g/ml) for cell isolation. The following formula can be used to calculate the volumes required to obtain a solution of the desired density.

$$Vy = Vi \frac{(P1 - P)}{(P - Py)}$$

wherein
  Vy=Volume of diluting medium (ml)
  Vi=Volume of stock PERCOLL™ (ml)
  P1=density of stock solution (g/ml)
  Py=density of diluting medium (g/ml)
  P=density of diluted solution produced (g/ml)

TABLE 1

The preparation of several densities of PERCOLL™ solution for the measurement of cancer cell densities.

| Stock Solution CP1 = 1.123 (g/m) | 0.15M NaCl (ml) | Solution density (g/ml) |
|---|---|---|
| 70 | 28 | 1.090 |
| 60 | 40 | 1.077 |
| 50 | 47 | 1.067 |
| 40 | 56 | 1.056 |
| 30 | 69 | 1.043 |
| 20 | 80 | 1.031 |

The density of the cancer cells is measured as follows:

The cancer cell lines used were obtained from commercial suppliers (e.g., the American Type Culture Collection). The LNCaP, TSU, and Hepatoma $G_2$ cell lines were cultured in RPMI 1640 with 10% FBS and 5% $CO_2$ at 37° C. Cells in 5 ml of culture medium were layered on 5 ml of single PERCOLL™ solution with a known density and centrifuged at 400×g for 20 minutes at room temperature. The interface and the PERCOLL™ solution above any visible pellet were collected. The number of cells in this suspension were counted and used for the calculation of recovery. The data are presented in Table 2.

TABLE 2

Density Measurements of Cancer Cells

| Percoll density | Recovery (%) | | |
|---|---|---|---|
| (g/ml) | LNCaP | TSU | Hepatoma $G_2$ |
| 1.031 | 10.0 | 10.0 | 10.0 |
| 1.043 | 20.5 | 15.0 | 17.0 |
| 1.056 | 25.0 | 20.5 | 24.0 |
| 1.067 | 76.0 | 84.5 | 85.0 |
| 1.077 | 76.5 | 98.5 | 98.0 |
| 1.090 | 76.0 | 98.5 | 98.0 |

As can be seen in Table 2, 76% to 85% of the cancer cells are recovered using a gradient with a density of 1.067 g/ml. With Hepatoma $G_2$ and TSU cells, an additional 13% to 14% cell recovery could be obtained using gradients with a density of 1.077 g/ml. No additional recovery of cells was found with LNCaP cells at the higher density.

EXAMPLE 2

This example illustrates a method of separation of prostatic cancer cells using a single density gradient column.

Twenty ml of fresh blood was taken in two tubes. The blood was diluted 1:2 with phosphate buffered saline (PBS). Thirty ml of the diluted blood containing $2.3 \times 10^5$ LNCaP cells (prostate cancer cells) were layered on 15 ml of a PERCOLL™ gradient with a density of 1.068 g/ml (Gradient I in FIG. 1). The gradient column was centrifuged at 400×g for twenty minutes at room temperature.

The cells at the interface between the blood plasma and the PERCOLL™ medium were carefully removed to a new tube. Forty ml of PBS was added into the new tube and mixed. The PBS diluted cells were centrifuged at 250×g for five minutes. The resulting pellet was suspended in 50 μl of 0.1% bovine serum albumin (BSA) solution.

The cell suspension thus prepared was smeared on slides as spots, each with 10 μl of the suspension. The slides were allowed to air-dry for two hours. The cells were fixed with 95% ethanol for fifteen minutes, and then with modified Carnoy's fixative for ten minutes. The slide was stored in 75% ethanol at 4° C. until used.

The above experiment was repeated nine more times, each time with a fresh blood sample. The average recovery of the prostate cancer cells in the ten experiments was 76–86%.

EXAMPLE 3

This example illustrates the method of separation of prostatic cancer cells using a higher single density gradient column. (See FIGS. 1 and 2A).

The pellet from the 1.068 g/ml density gradient (Gradient I in FIG. 1) of Example 2 was resuspended in the plasma fraction from Example 2, and layered on a higher density gradient column containing 10 ml of FICOLL™ medium having a density of 1.083 g/ml (Gradient II in FIG. 2A). The density gradient column was centrifuged at 400×g for twenty minutes at room temperature.

The cells at the interface between the blood plasma and the medium having a density of 1.083 g/ml were carefully removed with a cell transfer pipette and placed in a new tube. Forty ml of PBS was added to the interface cells and mixed. The PBS diluted cells were then centrifuged at 250×g. The resulting pellet was suspended in 0.5 ml of 0.1% by weight BSA solution. The white blood cells were counted using a light microscope.

Thirty μl of mouse anti-human CD45, CD19, CD3, CD14 monoclonal antibody (Sigma Chemical Co.), respectively, and 10 μl of glycophorin A monoclonal antibody (Dako, Inc.) were added to the cell suspension and the tube was incubated on ice for thirty minutes. The cell suspension was spin down and the supernatant was aspirated. The cell pellet was resuspended with $8 \times 10^7$ magnetic beads coated with anti-mouse IgG antibody (Dynal, Inc.) in 2 ml of PBS-BSA. The cells and beads were incubated at 4° C. for 30 minutes while rotating the tube at 10 rpm/minute. The cell-monoclonal antibody-mouse IgG-magnetic bead complexes were removed using a magnetic particle concentrator. The remaining cells were collected on a slide. The slide was prepared and the cells were fixed as described above in Example 2.

EXAMPLE 4

This example illustrates the efficiency of the procedure described in Example 2 for isolating prostate cancer cells from blood.

Blood samples were subjected to the procedure set forth in Example 1, except that the centrifugation was for twenty minutes instead of thirty minutes.

The total number of cells, the number of cells at the interface, the number of cells at the bottom of the gradient were measured, and the number of cells lost was determined. The data are set forth in Table 3.

TABLE 3

The Efficacy of Isolation of Prostatic Cancer Cells Using a Single Density Gradient

|  | Prostatic Cancer LNCaP P100 | Cell Lines TSU wt |
| --- | --- | --- |
| Total Cell Counts | $2.3 \times 10^5$ | $1.00 \times 10^7$ |
| Counts of Cells at Interface | $1.75 \times 10^5$ | $8.45 \times 10^6$ |
| (% Recovery) | (76%) | (84.5%) |
| Counts of Cell at Bottom | Few cells | $1.50 \times 10^5$ |
| (higher density cells %) | (~1.0%) | (15%) |
| Counts of Cells Lost* | $5.5 \times 10^4$ | $5.00 \times 10^4$ |
| (% loss) | (23%) | (0.5%) |

*Includes cells that were stuck on the tube wall and that were broken during the separation and wash.

EXAMPLE 5

This example illustrates the efficiency of the procedure illustrated in Example 3 for isolating prostate cancer cells from blood.

Blood samples were subjected to the procedure set forth in Example 2, except that the centrifugation was for twenty minutes.

The total number of cells, the number of cells at the interface and the number of cells at the bottom of the gradient were measured, and the number of cells lost was determined. The data are set forth in Table 4.

TABLE 4

The Efficacy of Isolation of Prostatic Cancer Cells Using a Secondary Density (1.083 g/ml) Gradient

|  | Prostatic Cancer LNCa P100 | Cell Lines TSU wt |
| --- | --- | --- |
| Total Cell Counts* | $2.3 \times 10^3$ | $1.50 \times 10^4$ |
| Counts of Cells at Interface | $1.87 \times 10^3$ | $1.45 \times 10^4$ |
| (% Recovery) | (81.3%) | (96.6%) |
| Counts of Cell at Bottom | No detection | No detection |
| (higher density cells %) | (~0%) | (~0%) |
| Counts of Cells Lost** | $4.5 \times 10^2$ | $5.00 \times 10^2$ |
| (% loss) | (~18.7%) | (~3.4%) |

*The cell suspension was the collection from the tube bottom of single gradient (1.068 g/ml) separation.
**Includes cells that were stuck on the tube wall and that were broken during the separation and wash.

EXAMPLE 6

This example illustrates a method of culturing cancer cells. LNCaP cells were counted and added into normal adult blood. The methods illustrated in Examples 2 and 3 were used for isolation of LNCaP cells in the artificial blood. The LNCaP cells isolated from the artificial blood were cultured in the growth medium RPMI 1640 supplemented with 10% serum and additional factor. The culture medium was changed every three days. The cultured cells showed positive immunostaining PSA and PSAP, and the number of cells in each flask increased with time in culture.

EXAMPLE 7

This example illustrates the identification of LNCaP cells or prostatic cancer cells from patients blood by fluorescent in situ hybridization (FISH) with PSA-mRNA, PSMA-mRNA and chromosome centromere probes.

Oligonucleotide probes specific for PSA-mRNA, PSMA-mRNA and the centromeres of chromosomes 7 and 18 were synthesized and conjugated with fluorescent dyes such as fluorescein, cy3 and cy5. The probe for chromosome centromere 8 was from a commercial source (Vysis).

The cancer cells isolated, fixed and stored by the method described in Examples 1 and 2 were pretreated in the solution of 0.1 M HCl—0.1% Triton X-100 for thirty minutes at room temperature, and dehydrated in series grades of ethanol at 75%, 85% and 95% for two minutes in each grade. The samples were air dried.

The FISH "Cocktail" comprises FISH buffer which mainly includes 25% Formamide and 4×SS (for oligomer probes) or 50% Formamide and 1×SSC (for commercial probes), 20 μg/ml PSA-mRNA probe and PSMA-mRNA probe, and 25 μg/ml chromosome 7, 8 and 18 centromere probes. Ten μl of FISH "Cocktail" were added on to each slide, under a coverslip. The samples were denatured at 80° C. for ten minutes and incubated at 42° C. for two hours. The slides were washed in 1×SSC at 70° for ten minutes. Ten μl of antifade mounting medium containing 0.2 μg/ml diamidino phenylindole (DAPI) were used for counterstaining. After counterstaining, the samples were examined under a fluorescent microscope. The chromosome 7 centromeres (which are multiploid) exhibited green stain, and the nucleus was stained in blue with DAPI.

The chromosome 8 centromeres (which are tetraploid) exhibited yellow stain, and the nucleus was stained in blue with DAPI.

The chromosomal centromeres were counted and the data are set forth in Table 5.

TABLE 5

Aneuploidy of Chromosome 7 and 8 in the Nucleus of LNCaP Cell from Culture and from Cancer Cells Isolated from Cancer Patient's Blood

| | Chromosomal Centromere 7 | | Chromosomal Centromere 8 | |
|---|---|---|---|---|
| Cell No. | LNCaP | Patient cancer cell | LNCaP | Patient cancer cell |
| 1 | 14 | 8 | 14 | 8 |
| 2 | 4 | 8 | 4 | 8 |
| 3 | 7 | 4 | 7 | 4 |
| 4 | 4 | 4 | 4 | 4 |
| 5 | 4 | 4 | 3 | 3 |
| 6 | 4 | 8 | 4 | 8 |
| 7 | 4 | 8 | 4 | 8 |
| 8 | 5 | 4 | 3 | 3 |
| 9 | 8 | 3 | 7 | 4 |
| 10 | 2 | 4 | 3 | 4 |

EXAMPLE 8

This example illustrates the identification of LNCaP cells or prostatic cancer cells from patients' blood by immunocytochemistry stain, as well as by chromosomal centromere 7 and 8 detection. The cancer cells enriched, isolated, fixed and stored as described in Examples 2 and 3 were stained by immunocytochemistry with primary antibodies against PSA and PAP, and secondary antibodies conjugated by fluorescent dyes. After immunocytochemistry staining, the samples were treated by 1% paraformaldehyde for 10 minutes at room temperature. The paraformaldehyde treatment provides for post-fixation of the cancer cells before fluorescent in situ hybridization (FISH) as well as crosslinking the antibodies and antigens and making the complex more stable during the FISH procedures. The slides were pre-treated by the solution of 0.1 M HCl 0.1% Triton X-100 for twenty minutes at room temperature and then dehydrated by 75%, 85% and 95% ethanol for two minutes in each grade. The slides were air dried.

The FISH cocktail fluid was prepared for chromosomal centromere 7 and 8 stain. The "Cocktail" comprised FISH buffer which contained 50% formamide and 2× SSC, and chromosomal centromere 7 and 8 DNA probes conjugated by fluorescent dyes. The cells, covered by 10 μl FISH "Cocktail" and a coverslip, were denatured at 80° C. for five minutes, and incubated at 42° C. for two to three hours. The slides were washed in 1×SSC for ten minutes at 60° C. Ten μl of an antifade mounting medium containing of 0.2 μg/ml DAPI were used for counterstaining. The samples were examined under a fluorescent microscope.

LNCaP cells immunofluorescently stained for Prostate Specific Antigen (PSA) exhibited green stain that represented the immunoreaction of PSA antibody in the cytoplasm.

LNCaP cells showed the immunofluorescent stain for the cell nucleus, as exhibited by the blue stain (DAPI).

LNCaP cells stained by immunocytochemistry with Prostatic Specific Acidic Phosphatase (PSAP) antibody showed the stain in the cytoplasm, while the blue stain showed the nucleus stained with DAPI.

Prostatic cells from the blood of prostatic cancer patients were stained in the cytoplasm (green) by immunochemistry with PSA antibodies, and then stained by FISH with chromosome centromere 7 (blue) and chromosome centromere 8 (red) probes in the nucleus.

EXAMPLE 9

This example illustrates the efficiency of enriching and isolating cancer cells by the method described in Examples 2 and 3.

Blood samples were reconstituted with LNCaP cells at varying ratios of white blood cells (WBC) to LNCaP cells. The cell recovery data set forth in Tables 6 and 7 confirm that the cancer cells are recoverable at high recovery percentages.

TABLE 6

Recovery of LNCaP Cells from Reconstituted Blood

| | | | Recovery of LNCaP, | |
|---|---|---|---|---|
| WBC:LNCaP | WBC | LNCaP | Counts | % |
| 500:1 | $2.76 \times 10^7$ | $6.5 \times 10^4$ | $5.5 \times 10^4$ | 84.6 |
| 1000:1 | $2.76 \times 10^7$ | $3.2 \times 10^4$ | $2.7 \times 10^4$ | 84.6 |
| 10000:1 | $2.76 \times 10^7$ | $3.2 \times 10^3$ | $2.8 \times 10^3$ | 86.2 |
| 0:20000 (control) | 0 | $2.3 \times 10^5$ | $1.8 \times 10^5$ | 78.3 |

TABLE 7

Recovery of prostatic cancer cells (LNCaP) in the reconstituted blood

| Sample No. | Quantity of Blood | WBC Counts | LNCaP | Cell Counts | Recovery |
|---|---|---|---|---|---|
| 51-9B3329 | 9.0 ml | $1.57 \times 10^8$ | ~100 | 85 | 85% |
| 51-5B3320 | 9.0 ml | $1.47 \times 10^8$ | ~100 | 80 | 80% |
| 51-0B3340 | 9.0 ml | $1.78 \times 10^8$ | ~100 | 97 | 97% |
| 51-0B3337 | 9.0 ml | $1.70 \times 10^8$ | ~100 | 95 | 95% |
| 51-0B3314 | 9.0 ml | $6.64 \times 10^7$ | ~100 | 82 | 82% |
| 51-7B3333 | 9.0 ml | $1.26 \times 10^8$ | ~100 | 94 | 94% |
| 51-0B3323 | 9.0 ml | $1.09 \times 10^8$ | ~100 | 90 | 90% |
| 51-6B3339 | 9.0 ml | $7.84 \times 10^7$ | ~100 | 96 | 96% |
| 51-2B3330 | 9.0 ml | $2.32 \times 10^8$ | ~100 | 75 | 75% |

TABLE 7-continued

Recovery of prostatic cancer cells (LNCaP) in the reconstituted blood

| Sample No. | Quantity of Blood | WBC Counts | LNCaP | Cell Counts | Recovery |
|---|---|---|---|---|---|
| 51-8B3310 | 9.0 ml | 1.59 × 10⁸ | ~100 | 90 | 90% |
| N = 10 | 9.0 ml | 1.42 × 10⁸ | ~100 | 88.4 | 88.4% |

The LNCaP cells isolated from the reconstituted blood had less than 1% of the original WBC concentration. The components of contamination were in the following order: monocytes>lymphocytes>eosinophils. The LNCaP cells isolated from the reconstituted blood have been found to grow in RPMI 1640 culture medium. The WBC contamination can be lowered by changing the culture medium after 3 days.

EXAMPLE 10

This example illustrates the identification of LNCaP cells or prostatic cancer cells from patients' blood by the combination of immunocytochemistry stain with cytokeratin monoclonal antibody, FISH with chromosomal centromere 7 and 18 probes, and PSMA mRNA probe.

The sample is fixed with 100% acetone at room temperature for two to three minutes. The slides are air-dried, and stored at room temperature in a slide box. The slides are incubated in 0.1M Tris washing buffer at room temperature for ten minutes, and the liquid is removed from the surface of the slides. Twenty five $\mu$l of FITC conjugated Anti-Cytokeratin (CAM5.2) monoclonal antibody (Becton-Dickinson, San Jose, Calif.; Cat. 347653) (1:2 dilution) is added onto the slides. The slides are incubated with a coverslip in a humid box at 37° C. for one hour. The slides are uncovered and washed in the 0.1 M Tris washing buffer at room temperature for ten minutes. The slides are then air-dried in a dark area.

The 1% paraformaldehyde with 0.1 M MgC12 is prepared and pre-cooled on ice. 1.0 ml of the 1% paraformaldehyde is dropped on the sample area. The sample is fixed at room temperature for 2–5 minutes. The fixative is removed from the surface of the slide, and the slide is air-dried at room temperature.

The FISH mixture (per sample) is prepared according to the following:

| | | |
|---|---|---|
| FISH buffer (Oncor) 9.0 $\mu$l | | |
| Cy3-Chromosomal centromere probe 18 | 28 ng | 0.5 $\mu$l |
| Cy3 conjugated PSMA-mRNA probe | 25 ng | 0.5 $\mu$l |
| Cy5-PSA-mRNA probe | 25 ng | 0.5 $\mu$l |
| Cy5-Chromosomal centromere probe 7 | 28 ng | 0.5 $\mu$l |
| Cy5-Chromosomal centromere probe 8 | 28 ng | 0.5 $\mu$l |

The FISH mixture is added onto the sample area. The coverslip is added and sealed with rubber cement. The sample is denatured at 85° C. for seven minutes, and the slide is incubated at 42° C. for two hours. The slide is washed in 1×SSC at 60° C. for five minutes, and the sample is air-dried at room temperature. The sample is counterstained with DAPI, and the slide is examined under a fluorescent microscope.

The results are summarized in Table 8.

TABLE 8

Detection of five prostatic cancer cell lines with cytokeratin immunocytochemistry staining and fluorescent in situ hybridization (FISH) of prostatic specific membrane antigen (PSMA) mRNA probe and chromosomal centromere 8 and 18 probes as well as DAPI nucleus staining (Percentage of positive staining).

| Cancer cell line | Immunocyto-chemistry | PSMA-mRNA | Chromosome 8 & 18 | DAPI |
|---|---|---|---|---|
| LNCaP | 100% | 100% | aneuploid (95–100%) | 100% |
| TSU-PRI | 100% | 100% | aneuploid (95–100%) | 100% |
| DUMS | 100% | 100% | aneuploid (95–100%) | 100% |
| PC-3 | 100% | 100% | aneuploid (95–100%) | 100% |
| PPC-1 | (—) | (—) | aneuploid (95–100%) | 100% |

The prostatic cancer cell is stained with Cy3 conjugated Prostatic Specific Membrane Antigen (PSMA) mRNA probe in the cytoplasm. The cell shows four greenish chromosomal centromere 7 signals in the nucleus stained by human 7 chromosomal centromere probe conjugated by fluorescein. The nucleus is stained with blue DAPI.

Another prostatic cancer cell has greenish cytokeratin stain in the cytoplasm and chromosome 8 autopolyploidy signals (four red spots) in the nucleus stained by DAPI. A white blood cell exhibits a blue nucleus with two chromosomal 8 signals (the normal chromosomal number).

EXAMPLE 11

This example illustrates the successful isolation and identification of prostate cancer cells from the blood of advanced prostate cancer patients by using the procedure in Example 2.

The patient number, the volume of blood samples collected, and the number of prostate cancer cells isolated, are set forth in Table 9.

TABLE 9

Collection of Prostatic Cancer Cells from the Blood of Advanced Cancer Patients

| Patient No. (N = 13) | Blood Quantity (ml) | Prostatic Cancer Cells (counts) |
|---|---|---|
| PC253 | 10 | 200 |
| PC254 | 20 | 140 |
| PC255 | 27 | 260 |
| PC256 | 9 | 6 |
| PC257 | 27 | 90 |
| PC258 | 15 | 40 |
| PC259 | 27 | No detection |
| PC260 | 22 | Fail to spin |
| PC261* | 15 | No detection |
| PC262* | 15 | No detection |
| PC263 | 7.5 | No detection |
| PC264 | 16 | No detection |
| PC265 | 9 | 20 |

*Control sample from normal adult blood

EXAMPLE 12

This example illustrates the successful isolation and identification (see the procedure in example 10) of prostate cancer cells from the blood of advanced prostate cancer patients.

In experiment I, the parallel study, the same sample was aliquoted into two equal parts and processed by same procedure. The patient number, the volume of blood sample collected, and the number of prostate cancer cells isolated, are set forth in table 10. The conclusion of the parallel study is that the isolation procedure is reproducible.

In experiment II, the storage study, the same sample was aliquoted into two equal parts and processed by same procedure. The samples in the Group A were processed within 24 hours and the samples in the Group B were processed after 72 hours storage at 4° C. The patient number, the volume of blood sample collected, and the number of prostate cancer cells isolated, are set forth in table 11. The conclusion from the storage study is that cancer cells were generally not preserved after 72 hours storage. In the one case wherein the cells were preserved after 72 hours storage, the cancer cells are smaller in size (approximately the size of monocytes), but with very typical and very intensive cytokeratonal system staining in the cytoplasm.

TABLE 10

Detection of Prostatic Cancer cells From Blood of Advanced Cancer Patients

Experiment I:

| Series No. | Age | PSA Quant. Bld. (U/L) | (ml) | | | Total No. |
|---|---|---|---|---|---|---|
| #1 | 58 | 19.9 | 20 | 3 | 4 | 7 |
| #2 | 58 | 81.1 | 18 | 2 | 3 | 5 |
| #3 | 72 | 76.0 | 18 | 5 | 4 | 9 |
| #4 | 66 | 44.9 | 15 | 2 | 2 | 4 |
| #5 | 69 | <0.1 | 20 | 1 | 2 | 3 |
| #6 | ? | 18.6 | 18 | 2 | 2 | 4 |
| #7 | 63 | 388.2 | 20 | 2 | 3 | 5 |
| #8 | 78 | 212.6 | 20 | 6 | 4 | 10 |
| #9 | 74 | 379.1 | 20 | 1 | 5 | 16 |
| | | | | | 1 cluster | 2 cluster |
| #10 | 67 | 61.7 | 20 | 2 | 1 | 3 |
| #11 | 71 | 182.6 | 20 | 1 | 1 | 2 |
| #12 | 42 | 4.4 | 20 | 0 | 0 | 0 |
| #13 | 53 | 85.7 | 20 | 8 | 7 | 15 |
| #14 | 59 | 37.7 | 20 | 0 | 0 | 0 |
| #15 | 59 | 6.1 | 20 | 0 | 0 | 0 |
| #16 | 58 | 337.3 | 15 | 5 | 5 | 10 |
| #17 | 67 | 14.69 | 20 | 0 | 1 | 1 |
| #18 | 81 | 17.5 | 20 | 11 | 12 | 23 |
| #19 | 72 | 9.7 | 20 | 0 | 0 | 0 |
| #20 | 81 | 61 | 20 | 1 | 2 | 3 |
| #21 | 54 | 43 | 20 | 3 | 4 | 7 |
| #22 | 61 | <0.1 | 18 | 0 | 0 | 0 |
| #23 | 69 | 1.15 | 20 | 0 | 0 | 0 |
| #24 | 61 | 44.3 | 18 | 0 | 0 | 0 |
| #25 | 61 | 25.1 | 16 | 1 | 1 | 2 |

* The same sample was aliquoted into two equal parts and processed by same procedure.

TABLE 11

Detection of Prostatic Cancer Cells From Blood of Advanced Cancer Patients

Experiment II:

| Series No. | Age | PSA Quant. Bld. (U/L) | (ml) | Cancer cells Group A | Group B | Total No. |
|---|---|---|---|---|---|---|
| #18 | 81 | 100 | 16 | 12 | 12 | 24** |
| #26 | 58 | 44 | 20 | 0 | 0 | 0 |
| #27 | 72 | ? | 15 | 0 | 0 | 0 |
| #1 | 58 | 52.6 | 20 | 2 | 0 | 2 |
| #2 | 68.3 | 72 | 20 | 3 | 0 | 3 |
| #7 | 63 | 381.5 | 20 | 2 | 0 | 2 |
| #13 | 53 | 26.2 | 20 | 4 | 0 | 4 |

TABLE 11-continued

Detection of Prostatic Cancer Cells From Blood of Advanced Cancer Patients

Experiment II:

| Series No. | Age | PSA Quant. Bld. (U/L) | (ml) | Cancer cells Group A | Group B | Total No. |
|---|---|---|---|---|---|---|
| #16 | 58 | 23.2 | 20 | 0 | 0 | 0 |
| #25 | 61 | 24.1 | 20 | 2 | 0 | 2 |
| #27 | 58 | 14.6 | 20 | 1 | 0 | 1 |

**The cancer cells are smaller in size (approximately the size of monocytes), but with very typical and very intensive staining cytokeratonal system in the cytoplasm.

EXAMPLE 13

This example illustrates a method of separation of prostatic cancer cells using a single density gradient column.

Blood samples were subjected to the procedure as set forth in Example 2, except that the centrifugation of the gradient column with a density of 1.068 g/ml was carried out at 400×g for 30 minutes at room temperature, rather than for 20 minutes. The slides were prepared as described in Example 2.

The experiment was repeated nine more times, each time with a fresh blood sample. The average recovery of the prostate cancer cells in the ten experiments is 70–80%.

EXAMPLE 14

This example illustrates a method of separation of prostatic cancer cells using a double density gradient column.

The pellet from the density gradient of Example 13 is resuspended in the plasma fraction from Example 13, and layered on a double density gradient column containing 10 ml of FICOLL™ medium having a density of 1.083 g/ml and 5 ml of FICOLL™ medium having a density of 1.077 g/ml. The suspension is layered onto the column so that it is in contact with the medium of lower density, which in turn is in contact with the higher density medium. Thus, using the left side of FIG. 2B for reference, Gradient III has a density of 1.077 g/ml, and Gradient II has a density of 1.083 g/ml. The density gradient column is centrifuged at 400×g for 30 minutes at room temperature.

Using the right side of FIG. 2B for reference, the cells at the interface (Interface II between the blood plasma and the Gradient II and III) were carefully removed with a cell transfer pipette and placed in a new tube. Forty ml of PBS was also added to the new tube and mixed. The PBS diluted cells were then centrifuged at 250×g. The resulting pellet was suspended in 2 ml of 0.1 wt. % BSA solution. The white blood cells were counted using a light microscope.

CD45-Dynalbeads were added to the above cell suspension (about 3 beads per 1 WBC were used). The cell suspension was incubated with the Dynalbeads for 30 minutes at 4° C. with gentle shaking. The tube containing the cells and the beads was placed in a magnetic particle concentrator (Dynal Corp.) and the cells in suspension were pipetted into a new tube leaving the beads and attached blood cells held in place in the tube by the magnetic particle concentrator.

The cell suspension was centrifuged at 250×g. The pellet obtained was resuspended in 30 μL of 1 wt. % BSA solution. The cell suspension thus prepared was smeared on slides as spots, each with 10 μL of the suspension. The slides were allowed to air dry for two hours. The cells were fixed with 95% ethanol for 10–15 minutes, and then with modified Carnoy's fixative.

EXAMPLE 15

This example illustrates the efficiency of the procedure illustrated in Example 13 for isolating prostate cancer cells from blood.

Blood samples are subjected to the procedure set forth in Example 14, except that centrifugation of the double density gradient column is performed for 20 minutes instead of 30 minutes.

The total number of cells, the number of cells at the interface, the number of cells at the bottom, and the number of cells lost are measured. The data are set forth in Table 12.

TABLE 12

Isolation of prostatic cancer cells using a double density gradient.

|  | Prostatic Cancer LNCaP P100 | Cell Lines TSU wt |
|---|---|---|
| % cells at interface* | ~1% | 14.5% |
| % cells at the bottom* | 0 | ~1% |
| % cells lost | 0 | 0 |

*This column contains cancer cells that "leaked" from the 1.068 g/ml gradient column.

EXAMPLE 16

This example illustrates the enrichment of prostatic cancer cells using a double density gradient column.

Twenty ml of fresh blood is taken into two tubes. The blood is diluted 1:2 PBS. Thirty ml of the diluted blood is layered on top of a double density gradient column which has an upper layer of 10 ml of 1.068 g/ml Histopaque™ (Sigma Chemical Co.) and a lower layer of 10 ml of 1.083 g/ml Histopaque™ as illustrated in the left side of FIG. 3. The column is centrifuged at 400×g for 30 minutes at room temperature to form 6 layers as shown in the right side of FIG. 3.

After centrifugation, Interface I and Gradient I are carefully removed and placed in another tube, and Interface II and Gradient II are also carefully removed and placed in yet another tube.

Forty ml of PBS is added to the tube containing the Interface I and Gradient I, and mixed. The PBS diluted cells are centrifuged at 250×g for 5 minutes. The resultant pellet is suspended in 50 μl of 1% BSA solution to form a cell suspension that is smeared on a slide as a spot. The slide is air dried for at least two hours. The cells are fixed with 95% ethanol for 15 minutes, and then with modified Carnoy's fixative for 10 minutes. The slide is stored in 75% ethanol at 4° C. until used.

As noted above, Interface II and Gradient II are also carefully removed to a new tube. Forty ml of PBS is added to the new tube and mixed. The PBS diluted cells are centrifuged at 250×g for 5 minutes. The resultant pellet is suspended in 2 ml of 1% BSA solution. CD45-Dynalbeads are added to the cell suspension (about 3–10 beads per white blood cell (leukocyte)), and the suspension was incubated with the Dynalbeads for 30 minutes at 4° C. with gentle rotation.

The tube containing the cells and beads is placed on a Dynal magnetic concentrator. The concentrator is operated to attract the beads and attached blood cells to the wall of the tube.

The suspension containing the cancer cells is pipetted into another tube. Slides are prepared as described above.

EXAMPLE 17

This example illustrates the efficiency of the procedure described in example 16 for isolating prostatic cancer cells from blood. The procedure described in Example 16 is repeated nine more times, each time with a fresh blood sample containing LNCaP cells. The average recovery of the prostatic cancer cells from Interface I and Gradient I is about 70–80%. The average recovery of the prostatic cancer cells from Interface II and Gradient II is about 5–10%.

All of the nucleic acid sequences listed in this application are set forth in the 5'-3' configuration.

All of the references cited herein including patents and publications are hereby incorporated in their entireties by reference.

While the invention has been described and disclosed herein in connection with certain preferred embodiments and procedures, it is not intended to limit the invention to those specific embodiments. Rather it is intended to cover all such alternative embodiments and modifications as fall within the spirit and scope of the invention.

What is claimed is:

1. A method for enriching cancer cells in a bodily fluid sample comprising cancer cells and non-rare cells comprising:

(a) obtaining the sample comprising cancer cells and non-rare cells;

(b) subjecting the sample to multiple density gradient separation comprising a first density gradient and a second density gradient, wherein the second density gradient is greater than the first density gradient, and producing a first fluid comprising an increased concentration of cancer cells of a first density, and a second fluid comprising an increased concentration of cancer cells of a second density, wherein the second density is greater than the first density;

wherein subjecting the sample to multiple density gradient separation includes producing a plasma layer, a first interface layer, a first gradient layer, a second interface layer, a second gradient layer, and a cell pellet;

wherein producing the first fluid includes combining the first interface layer and the first gradient layer and forming a first suspension; and wherein producing the second fluid includes combining the second interface layer and the second gradient layer and forming a second suspension;

(c) subjecting said second fluid comprising the second suspension to a binding agent that binds non-rare cells;

(d) removing the bound non-rare cells from the second fluid to provide a second fluid enriched with the greater density cancer cells, and (e) preparing a fluid enriched with the cancer cells of the first density and the cancer cells of the greater density by combining the cancer cells of the first density from the first fluid and the greater density cancer cells from the second fluid enriched with the greater density cancer cells.

2. The method of claim 1, wherein said cancer cells are alive during the course of said method.

3. The method of claim 1, wherein said cancer cells are epithelial cells.

4. The method of claim 3, wherein said epithelial cells are prostate cancer cells.

5. The method of claim 4, further comprising characterizing the prostate cells using at least one prostate-specific marker expressed by the prostate cells.

6. The method of claim 5, comprising detecting at least one of a prostate-specific antigen and a prostate-specific membrane antigen.

7. The method of claim 4, further comprising characterizing the prostate cells using a cytokeratin protein marker expressed by the prostate cells.

8. The method of claim 6, wherein at least one of the prostate-specific antigen and the prostate-specific membrane antigen is detected using a nucleic acid probe that specifically binds to the mRNA of said antigen.

9. The method of claim 8, wherein said probe is selected from the group consisting of SEQ. ID. Nos. 1, 2, and 6.

10. The method of claim 8, wherein said probe is selected from the group consisting of SEQ. ID. Nos. 3, 4, 7, and 8.

11. The method of claim 6, wherein at least one of the prostate-specific antigen and the prostate-specific membrane antigen is detected using an antibody that specifically binds to said antigen.

12. The method of claim 3, further comprising characterizing ploidy state of the epithelial cell using at least one centromere specific marker.

13. The method of claim 12, wherein the centromere specific marker comprises a nucleic acid probe that specifically binds to a complementary sequence of the centromere DNA.

14. The method of claim 13, wherein said probe comprises SEQ. ID. No. 5.

15. The method of claim 13, wherein said probe comprises SEQ. ID. No. 10.

16. The method of claim 1, wherein said binding agent comprises an antibody.

17. The method of claim 16, wherein said binding agent comprises at least two primary antibodies from animals that are capable of binding to different non-rare cell antigens.

18. The method of claim 16, wherein said binding agent comprises a primary antibody from an animal that binds to a non-rare cell, and a secondary anti-antibody from another species than the primary antibody, wherein said secondary anti-antibody binds to the primary antibody.

19. The method of claim 17, wherein the at least two primary antibodies are capable of binding to human non-rare cell antigens, and the binding agent further comprises secondary antibodies capable of binding to the two primary antibodies, wherein the primary antibodies are from a different species than the secondary antibodies.

20. The method of claim 1, wherein subjecting the sample to density gradient separation comprises using at least one density gradient medium having a density of no less than about 1.06 g/ml.

21. A method of detecting cancer cells in a fluid comprising cancer and non-rare cells, which method comprises providing a fluid enriched with cancer cells by the method of claim 1, and analyzing said fluid to detect said cancer cells.

22. A method of detecting prostate cancer cells comprising providing a fluid enriched with prostate cancer cells by the method of claim 4, and analyzing said fluid to detect the prostate cancer cells.

23. The method of claim 3, further comprising determining the number of chromosomes in the cancer cells.

24. The method of claim 4, further comprising determining the number of chromosomes in the prostate cancer cells.

25. The method of claim 23, including determining the presence of aneuploidy in the cancer cells.

26. The method of claim 3, comprising increasing by at least about 500-fold the concentration of the cancer cells compared to the concentration of the cancer cells to the non-rare cells in the fluid sample.

27. The method of claim 1, wherein the cancer cells are human liver cells, hepatoma cells, or hepatocarcinoma cells.

28. The method of claim 1, wherein said fluid is blood.

29. The method of claim 1 comprising subjecting the second fluid comprising an increased concentration of cancer cells of a second density to a binding agent that binds white blood cells and red blood cells, and removing the bound white blood cells and bound red blood cells from the second fluid to provide a second fluid enriched with the greater density cancer cells.

30. The method of claim 1, wherein the cells are alive during the course of said method.

31. The method of claim 1, wherein the non-rare cells comprise blood cells.

32. The method of claim 31, wherein the blood cells comprise leukocytes and red blood cells.

33. A cancer cell enriched fluid prepared in accordance with the method of claim 1.

34. The method of claim 1, wherein the first density gradient has a density in the range of about 1.068 g/mL to about 1.077 g/mL, and wherein the second density gradient has a density in the range of about 1.077 g/mL to about 1.085 g/mL.

35. The method of claim 3, wherein the epithelial cancer cells comprise breast cancer cells.

36. The method of claim 3, wherein the epithelial cancer cells comprise kidney cancer cells.

37. The method of claim 1, wherein subjecting the second fluid to the binding agent includes binding the white blood cells and/or red blood cells to magnetic beads.

* * * * *